(12) United States Patent
Ackermann et al.

(10) Patent No.: US 8,389,539 B2
(45) Date of Patent: Mar. 5, 2013

(54) AZACYCLIC DERIVATIVES

(75) Inventors: Jean Ackermann, Riehen (CH); Aurelia Conte, Basel (CH); Daniel Hunziker, Moehlin (CH); Werner Neidhart, Hagenthal-le-Bas (FR); Matthias Nettekoven, Grenzach-Wyhlen (DE); Tanja Schulz-Gasch, Ziefen (CH); Stanley Wertheimer, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 81 days.

(21) Appl. No.: 12/951,095

(22) Filed: Nov. 22, 2010

(65) Prior Publication Data

US 2011/0130417 A1 Jun. 2, 2011

(30) Foreign Application Priority Data

Dec. 1, 2009 (EP) ..................................... 09177653

(51) Int. Cl.
*A61K 31/438* (2006.01)
*C07D 221/20* (2006.01)
(52) U.S. Cl. ............. 514/278; 546/15; 546/16; 514/277
(58) Field of Classification Search .................... 546/16, 546/15; 514/278, 277
See application file for complete search history.

(56) References Cited

U.S. PATENT DOCUMENTS 8,039,480 B2 * 10/2011 Schudok et al. ............... 514/278
8,097,634 B2 * 1/2012 Ackermann et al. .......... 514/278

FOREIGN PATENT DOCUMENTS

| EP | 1683797 | 7/2006 |
|---|---|---|
| JP | 2001261679 | 9/2001 |
| WO | 2005/084667 | 9/2005 |

OTHER PUBLICATIONS

International Search Report mailed Apr. 6, 2011 in PCT/EP2010/068265.
Wang et al., Chemical Biology (2006) vol. 13 pp. 1019-1027.
Gregoire et al., Physiol. Review (1998) vol. 78 pp. 783-809.
Unger et al., Annual Review Med. (2002) vol. 53 pp. 319-336.
Large et al., J. Lipid. Res. vol. 39 (1998) pp. 1688-1695.
Hotamisigil, G. S., J. Clin. Invest. vol. 95 (1995) pp. 2409-2415.
Gao et al., Mol. Endocrinol. vol. 18 (2004) pp. 2024-2034.
Stanley et al., Physiol. Review vol. 85 (2005) pp. 1093-1129.
Oliver, M. F., QJM vol. 99 (2006) pp. 701-709.
Cusi et al., J. Cardiometab. Syndr. vol. 3 (2009) pp. 141-146.
Atgie et al., J. Physiol. Biochem. vol. 65 (2009) pp. 33-41.
Lewis, et al., Dig. Dis. Sci. vol. 55 (2010) pp. 560-578.

* cited by examiner

*Primary Examiner* — Golam M M Shameem
(74) *Attorney, Agent, or Firm* — George W. Johnston; Patricia S. Rocha-Tramaloni; Gene J. Yao

(57) ABSTRACT

Compounds of formula (I)

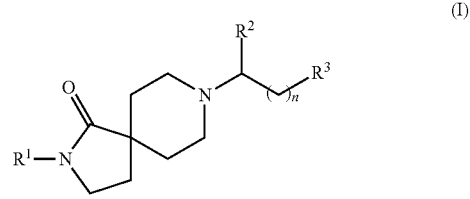

as well as pharmaceutically acceptable salts thereof can be used in the form of pharmaceutical compositions, wherein $R^1$, $R^2$, $R^3$ and n have the significance given in claim 1.

18 Claims, No Drawings

AZACYCLIC DERIVATIVES

PRIORITY TO RELATED APPLICATION(S)

This application claims the benefit of European Patent Application No. 09177653.4, filed Dec. 1, 2009, which is hereby incorporated by reference in its entirety.

FIELD OF THE INVENTION

The present invention is concerned with novel azacyclic spiro derivatives useful as HSL inhibitors for the treatment of diabetes.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess (Wang M. et al., Chem. Biol., 2006, 13, 1019-1027; Gregoire F. M. et al., Physiol. Rev., 1998, 78, 783-809). However, unlike TAG synthesis that also occurs at high levels in liver for very low density lipoprotein (VLDL) production, lipolysis for the provision of fatty acids as an energy source for use by other organs is unique to adipocytes. The release of free fatty acids (FFA) from TAG proceeds in an orderly and regulated manner (Unger R. H, Annu. Rev. Med. 2002, 53, 319-336; Duncan R. E. et al, 2007, Annu Rev Nutr, 27, 79-101; Jaworski K. Et al, 2007, Am J Physiol Gastrointest Liver Physiol, 293, G1-4), stimulated by catecholamines and regulated by hormones such as insulin, glucagon and epinephrine.

The most important enzyme in WAT believed responsible for hormone regulated hydrolysis of triglyceride is hormone sensitive lipase (HSL). This enzyme is also present in the liver, skeletal muscle, pancreas and adrenal glands. In the basal state, it has minimal activity against its substrate. Stimulation of adipocytes by hormones activates protein kinase A resulting in the phosphorylation of HSL and the lipid droplet coating protein perilipin. Phosphorylation of perilipin leads to its removal from the lipid droplet and migration of phosphorylated HSL from the cytosol to the lipid droplet where it catalyzes the hydrolysis of triglycerides (Wang M. et al., Chem. Biol., 2006, 13, 1019-1027).

Dysregulation of adipocyte lipolysis, resulting in elevated circulating non-esterified fatty acids (NEFA) is associated with obesity and co-morbidities including the development of type 2 diabetes (Unger R. H, Annu. Rev. Med. 2002, 53, 319-336). Obese or insulin resistant subjects have increased visceral adipose tissue depots. These depots contain elevated levels of HSL protein (Large, V. et al., 1998, J. Lipid. Res. 39, 1688-1695) and exhibit enhanced lipolytic activity as they are resistant to the insulin-mediated suppression of lipolysis. This results in increased plasma levels of free fatty acids, which further exacerbates insulin resistance due to the accumulation of triglycerides in tissues other than WAT such as liver, pancreas and muscle. The ectopic deposition of triglycerides results in pathological effects such as increased glucose production in the liver, decreased insulin secretion from the pancreas, and reduced glucose uptake and fatty acid oxidation in skeletal muscle. Thus, the elevated plasma levels of FFA due to increased HSL activity contributes to and worsens insulin resistance in obese and type 2 diabetic individuals. In addition, elevated FFA is related to increased production of the inflammatory cytokine TNF-alpha, by the adipose tissue (Hotamisigil, G. S., 1995, J. Clin. Invest. 95, 2409-2415). TNF-alpha further disrupts insulin signaling by the activation of serine kinases, such as JNK-1, which phosphorylated IRS-1 which depresses insulin signaling (Gao, Z. et. al., Mol Endocrinol, 2004, 18, 2024-2034). Thus, restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function. Inflammatory cytokine production would also be lessened, leading to further reductions in FFA production and improved insulin signaling. Elevated FFAs are also associated with increased cardiovascular risk, including atherosclerosis and myocardial dysfunction (Lopaschuk, et. al., Physiol Rev 2005, 85, 1093-129; Oliver, M F, QJM 2006, 99, 701-9) It has also been demonstrated that chronic low-dose lipid infusion in healthy patients induces markers of endothelial activation independent of its metabolic effects (Cusi, et. al., J. Cardiometab. Syndr. 2009, 3, 141-6). Here it was shown that modest lipid infusion elevates markers of endothelial activation-ET-1, ICAM-1, VCAM-1. Furthermore high lipolytic activity and elevated FFAs lead to increased insulin resistance and hypertension in hypertensive rats (Mauriege, et. al. J Physiol Biochem. 2009, 65, 33-41).

As HSL is a major hormone regulated lipase, it is known that during insulin resistant states, the ability of insulin to suppress lipolysis is reduced, and contributes to the increased FFA, ie. lipotoxicity. These fatty acids collect in the liver and lead to increased production of TAG, which are packaged into VLDLs which are secreted. There is also an accumulation of lipid in liver, leading to a fatty liver phenotype. Lipolysis is increased during diabetes and obesity which contributes to this phenotype. Therefore, reducing the activity of HSL would decrease the release of FFA to the blood, thus limiting the supply of FFA to the liver for TAG synthesis. Thus, HSL inhibitors could have beneficial effects as treatment of NAFLD (nonalkoholic fatty liver disease) and NASH (nonalkoholic steatohepatitis) (Jeffry R. Lewis et al, Dig Dis Sci 2010, 55: 560-578).

SUMMARY OF THE INVENTION

The present invention relates to a compound according to formula (I)

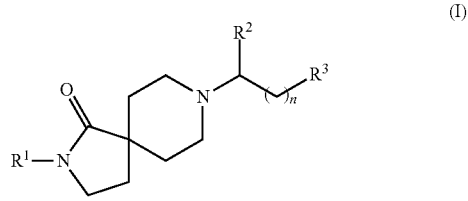

wherein $R^1$ is substituted phenyl, wherein substituted phenyl is substituted with one to three substituents independently selected from the group consisting of: alkyl, cycloalkyl, haloalkyl, hydroxy, alkoxy, hydroxyalkoxy, alkoxylakoxy, and haloalkoxy and, wherein substituted phenyl is optionally further substituted with one to two substituents independently selected from halogen;

$R^2$ is selected from the group consisting of: hydrogen, alkyl, cycloalkyl, phenyl, phenylalkyl, substituted phenyl or substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;

$R^3$ is selected from the group consisting of: —$R^4$, —C(OH)$R^5R^6$ and —C(O)NR$^7R^8$;

$R^4$ is selected from the group consisting of: phenyl, phenylcarbonyl, phenylalkyl, substituted phenyl, substituted phenylcarbonyl and substituted phenylalkyl, wherein substituted phenyl, substituted phenylcarbonyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;

one of $R^5$ and $R^6$ is selected from the group consisting of: hydrogen, alkyl and cycloalkyl and the other one is selected from the group consisting of: aminocarbonyl, phenyl, phenylalkyl, substituted phenyl or substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;

one of $R^7$ and $R^8$ is selected from the group consisting of: hydrogen, alkyl, cycloalkyl, hydroxyalkyl and alkoxyalkyl and the other is selected from the group consisting of: alkyl, cycloalkyl, hydroxyalkyl, alkoxyalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;

or $R^7$ and $R^8$ together with the nitrogen atom to which they are attached form pyrrolidinyl, piperidinyl, azepanyl, piperidazinyl, morpholinyl or thiomorpholinyl; and n is zero or 1;

or a pharmaceutically acceptable salt thereof.

DETAILED DESCRIPTION OF THE INVENTION

The term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl, isopropyl, butyl and isobutyl. Particularly preferred alkyl are methyl, ethyl, propyl and butyl.

The term "cycloalkyl", alone or in combination, signifies a cycloalkyl ring with 3 to 8 carbon atoms and preferably a cycloalkyl ring with 3 to 6 carbon atoms. Examples are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyl are cyclopropyl and cyclohexyl.

The term "alkoxy", alone or in combination, signifies a group of the formula alkyl-O— in which the term "alkyl" has the previously given significance. Examples are methoxy, ethoxy, n-propoxy, isopropoxy, n-butoxy, isobutoxy, sec-butoxy and tert-butoxy, preferably methoxy and ethoxy. A particularly preferred alkoxy is methoxy.

The term "hydroxyalkyl", alone or in combination, signifies an alkyl group as defined before, wherein one or more hydrogen is replaced by a hydroxy group. Examples of hydroxyalkyl are hydroxymethyl, hydroxyethyl, hydroxypropyl, hydroxymethypropyl and dihydroxypropyl. Preferred hydroxyalkyl are hydroxyethyl and hydroxymethylpropyl.

The term "halogen", alone or in combination, signifies fluorine, chlorine, bromine or iodine. Preferred halogen are fluorine and chlorine.

The term "haloalkyl", alone or in combination, signifies an alkyl group as defined before, wherein one or more hydrogen is replaced by a halogen. Examples of haloalkyl are fluoromethyl, difluoromethyl, trifluoromethyl, trifluoroethyl, trifluoromethylethyl or pentafluoroethyl. A preferred haloalkyl is trifluoromethyl.

The term "haloalkoxy", alone or in combination, signifies an alkoxy group as defined before, wherein one or more hydrogen attached to a carbon is replaced by a halogen. Examples of haloalkyl are fluoromethoxy, difluoromethoxy, trifluoromethoxy, trifluoroethoxy, trifluoromethylethoxy, trifluorodimethylethoxy or pentafluoroethoxy. A preferred haloalkoxy is trifluoromethoxy.

The term "hydroxy", alone or in combination, signifies the —OH group.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring. Examples are —$NH_2$, methylamino, ethylamino, dimethylamino, diethylamino, methyl-ethylamino, pyrrolidinyl, morpholinyl or piperidinyl, preferably —$NH_2$, dimethylamino and diethylamino and particularly —$NH_2$.

The term "protecting group" refers to groups which are used to block the reactivity of functional groups such as amino groups or hydroxy groups. Examples of protecting groups are tert-butyloxycarbonyl (Boc), benzyloxycarbonyl (Cbz), fluorenylmethyloxycarbonyl (Fmoc) or benzyl (Bn). Preferred protecting groups are tert-butyloxycarbonyl (Boc) and benzyl (Bn).

Cleavage of protecting group can be done using standard methods known by the man skilled in the art such as hydrogenation or in the presence of an acid, e.g. HCl or TFA, preferably HCl, or a base, e.g. triethylamine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particularly preferred pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred pharmaceutically acceptable esters of compounds of formula (I) are methyl and ethyl esters.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The present invention relates to a compound according to formula (I)

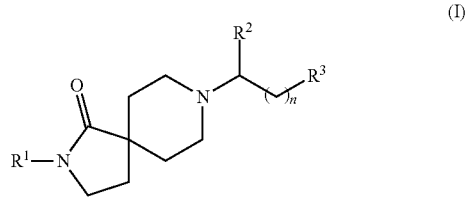

wherein
$R^1$ is substituted phenyl, wherein substituted phenyl is substituted with one to three substituents independently selected from the group consisting of: alkyl, cycloalkyl, haloalkyl, hydroxy, alkoxy, hydroxyalkoxy, alkoxylakoxy, and haloalkoxy and, wherein substituted phenyl is optionally further substituted with one to two substituents independently selected from halogen;
$R^2$ is selected from the group consisting of: hydrogen, alkyl, cycloalkyl, phenyl, phenylalkyl, substituted phenyl or substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
$R^3$ is selected from the group consisting of: —$R^4$, —C(OH)$R^5R^6$ and —C(O)NR$^7$R$^8$;
$R^4$ is selected from the group consisting of: phenyl, phenylcarbonyl, phenylalkyl, substituted phenyl, substituted phenylcarbonyl and substituted phenylalkyl, wherein substituted phenyl, substituted phenylcarbonyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
one of $R^5$ and $R^6$ is selected from the group consisting of: hydrogen, alkyl and cycloalkyl and the other one is selected from the group consisting of: aminocarbonyl, phenyl, phenylalkyl, substituted phenyl or substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
one of $R^7$ and $R^8$ is selected from the group consisting of: hydrogen, alkyl, cycloalkyl, hydroxyalkyl and alkoxyalkyl and the other is selected from the group consisting of: alkyl, cycloalkyl, hydroxyalkyl, alkoxyalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
or $R^7$ and $R^8$ together with the nitrogen atom to which they are attached form pyrrolidinyl, piperidinyl, azepanyl, piperidazinyl, morpholinyl or thiomorpholinyl; and
n is zero or 1;
or a pharmaceutically acceptable salt or ester thereof.

Further preferred is a compound according to formula (I) as described above or a pharmaceutically acceptable salt thereof, particularly a compound according to formula (I) as described above.

Also preferred is a compound according to formula (I), wherein
$R^1$ is substituted phenyl, wherein substituted phenyl is substituted with one to three substituents independently selected from the group consisting of: alkyl, cycloalkyl, haloalkyl, hydroxy, alkoxy, hydroxyalkoxy, alkoxyalkoxy and haloalkoxy, and wherein substituted phenyl is optionally further substituted with one to two substituents independently selected from halogen;
$R^2$ is selected from the group consisting of: hydrogen, alkyl, cycloalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
$R^3$ is selected from the group consisting of: —$R^4$, —C(OH) $R^5R^6$ and —C(O)NR$^7$R$^8$;
$R^4$ is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy; one of $R^5$ and $R^6$ is selected from the group consisting of: hydrogen, alkyl and cycloalkyl and the other is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy; one of $R^7$ and $R^8$ is selected from the group consisting of: hydrogen, alkyl, cycloalkyl, hydroxyalkyl and alkoxyalkyl and the other is selected from the group consisting of: alkyl, cycloalkyl, hydroxyalkyl, alkoxyalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;

or $R^7$ and $R^8$ together with the nitrogen atom to which they are attached form pyrrolidinyl, piperidinyl, azepanyl, piperidazinyl, morpholinyl or thiomorpholinyl; and n is zero or 1;

or a pharmaceutically acceptable salt thereof.

Also further preferred is a compound according to formula (I) as described above, wherein $R^1$ is substituted phenyl, wherein substituted phenyl is substituted with one to three substituents independently selected from cycloalkyl and haloalkoxy, and, wherein substituted phenyl is optionally further substituted with one to two substituents independently selected from halogen.

Furthermore preferred is a compound according to formula (I) as described above, wherein $R^1$ is substituted phenyl, wherein substituted phenyl is substituted with one to three substituents independently selected from cycloalkyl.

Particularly preferred is a compound according to formula (I) as described above, wherein $R^1$ is substituted phenyl, wherein substituted phenyl is substituted with cyclopropyl.

Further preferred is a compound according to formula (I) as described above, wherein $R^3$ is —C(OH)$R^5R^6$.

Further preferred is a compound according to formula (I) as described above, wherein one of $R^5$ and $R^6$ is hydrogen or alkyl and the other is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy.

Furthermore preferred is a compound according to formula (I) as described above, wherein one of $R^5$ and $R^6$ is hydrogen and the other is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy.

Particularly preferred is a compound according to formula (I) as described above, wherein one of $R^5$ and $R^6$ is hydrogen or alkyl and the other is phenyl or substituted phenyl, wherein substituted phenyl is substituted with one to three substituents independently selected from halogen.

Moreover preferred is a compound according to formula (I) as described above, wherein one of $R^5$ and $R^6$ is hydrogen and the other is phenyl or substituted phenyl, wherein substituted phenyl is substituted with one to three substituents independently selected from halogen.

Also preferred is a compound according to formula (I) as described above, wherein $R^3$ is —C(OH)$R^5R^6$ and n is zero.

Another preferred embodiment of the present invention is a compound according to formula (I) as described above, wherein $R^3$ is —C(O)NR$^7R^8$.

Also further preferred is a compound according to formula (I) as described above, wherein one of $R^7$ and $R^8$ is hydrogen or alkyl and the other one is selected from the group consisting of: alkyl, cycloalkyl, alkoxyalkyl, phenylalkyl, substituted phenyl and substituted phenylalkyl, wherein substituted phenyl and substituted phenylalkyl are substituted with one to three substituents independently selected from halogen and haloalkyl.

Furthermore preferred is a compound according to formula (I) as described above, wherein one of $R^7$ and $R^8$ is hydrogen and the other is selected from the group consisting of: alkyl, substituted phenyl and substituted phenylalkyl, wherein substituted phenyl and substituted phenylalkyl are substituted with one to three substituents independently selected from halogen and haloalkyl.

Also preferred is a compound according to formula (I) as described above, wherein $R^7$ and $R^8$ together with the nitrogen atom to which they are attached form pyrrolidinyl.

Another preferred embodiment of the present invention is a compound according to formula (I) as described above, wherein $R^4$ is selected from the group consisting of: phenyl, phenylalkyl and substituted phenyl, wherein substituted phenyl is substituted with one to three substituents independently selected from haloalkyl.

Furthermore preferred s a compound according to formula (I) as described above, wherein $R^4$ is selected from the group consisting of: phenyl, benzyl, phenylethyl, phenylpropyl and substituted phenyl, wherein substituted phenyl is substituted with trifluoromethyl.

Particularly preferred is a compound according to formula (I) as described above, wherein $R^4$ is phenyl.

Also preferred is a compound according to formula (I) as described above, wherein $R^2$ is selected from the group consisting of: hydrogen, alkyl and phenyl.

Furthermore preferred is a compound according to formula (I) as described above, wherein $R^2$ is hydrogen or alkyl.

Particularly preferred is a compound according to formula (I) as described above, wherein $R^2$ is hydrogen.

Also particularly preferred is a compound according to formula (I) as described above, wherein $R^2$ is alkyl.

Examples of a preferred compound according to formula (I) as described above is selected from the group consisting of:

2-(4-Cyclopropyl-phenyl)-8-(3-phenyl-propyl)-2,8-diaza-spiro[4.5]decan-1-one;

2-(4-Cyclopropyl-phenyl)-8-phenethyl-2,8-diaza-spiro[4.5]decan-1-one;

2-(4-Cyclopropyl-phenyl)-8-(4-trifluoromethyl-benzyl)-2,8-diaza-spiro[4.5]decan-1-one;

2-(4-Cyclopropyl-phenyl)-8-(1-phenyl-ethyl)-2,8-diaza-spiro[4.5]decan-1-one;

2-(4-Cyclopropyl-phenyl)-8-[1-(3-trifluoromethyl-phenyl)-ethyl]-2,8-diaza-spiro[4.5]decan-1-one;

2-(2-Chloro-4-cyclopropyl-phenyl)-8-(1-phenyl-ethyl)-2,8-diaza-spiro[4.5]decan-1-one;

2-(4-Cyclopropyl-phenyl)-8-(1-phenyl-propyl)-2,8-diaza-spiro[4.5]decan-1-one;

8-Benzyl-2-(4-trifluoromethoxy-phenyl)-2,8-diaza-spiro[4.5]decan-1-one;

2-[2-(4-Cyclopropyl-phenyl)-1-oxo-2,8-diaza-spiro[4.5]dec-8-yl]-N-ethyl-acetamide;

2-[2-(4-Cyclopropyl-phenyl)-1-oxo-2,8-diaza-spiro[4.5]dec-8-yl]-N,N-diethyl-acetamide;

N-Butyl-2-[2-(4-cyclopropyl-phenyl)-1-oxo-2,8-diaza-spiro[4.5]dec-8-yl]-acetamide;

2-[2-(4-Cyclopropyl-phenyl)-1-oxo-2,8-diaza-spiro[4.5]dec-8-yl]-N-(4-trifluoromethyl-benzyl)-acetamide;

2-[2-(4-Cyclopropyl-phenyl)-1-oxo-2,8-diaza-spiro[4.5]dec-8-yl]-N-(4-fluoro-phenyl)-acetamide;

2-(4-Cyclopropyl-phenyl)-8-(2-oxo-2-pyrrolidin-1-yl-ethyl)-2,8-diaza-spiro[4.5]decan-1-one;

N-Benzyl-2-[2-(4-cyclopropyl-phenyl)-1-oxo-2,8-diaza-spiro[4.5]dec-8-yl]-N-methyl-acetamide;
N-Cyclohexyl-2-[2-(4-cyclopropyl-phenyl)-1-oxo-2,8-diaza-spiro[4.5]dec-8-yl]-N-methyl-acetamide;
2-[2-(4-Cyclopropyl-phenyl)-1-oxo-2,8-diaza-spiro[4.5]dec-8-yl]-N-(3-methoxy-propyl)-acetamide;
N-Butyl-3-[2-(4-cyclopropyl-phenyl)-1-oxo-2,8-diaza-spiro[4.5]dec-8-yl]-propionamide;
3-[2-(4-Cyclopropyl-phenyl)-1-oxo-2,8-diaza-spiro[4.5]dec-8-yl]-N-(4-trifluoromethyl-benzyl)-propionamide;
3-[2-(4-Cyclopropyl-phenyl)-1-oxo-2,8-diaza-spiro[4.5]dec-8-yl]-N-(4-fluoro-phenyl)-propionamide;
N-Benzyl-3-[2-(4-cyclopropyl-phenyl)-1-oxo-2,8-diaza-spiro[4.5]dec-8-yl]-N-methyl-propionamide;
N-Cyclohexyl-3-[2-(4-cyclopropyl-phenyl)-1-oxo-2,8-diaza-spiro[4.5]dec-8-yl]-N-methyl-propionamide;
2-(4-Cyclopropyl-phenyl)-8-(2-hydroxy-2-phenyl-ethyl)-2,8-diaza-spiro[4.5]decan-1-one;
8-[2-(4-Chloro-phenyl)-2-hydroxy-ethyl]-2-(4-cyclopropyl-phenyl)-2,8-diaza-spiro[4.5]decan-1-one;
2-[2-(4-Cyclopropyl-phenyl)-1-oxo-2,8-diaza-spiro[4.5]dec-8-yl]-N-(4-fluoro-phenyl)-propionamide;
2-[2-(4-Cyclopropyl-phenyl)-1-oxo-2,8-diaza-spiro[4.5]dec-8-yl]-N-(4-fluoro-phenyl)-butyramide;
N-Butyl-2-[2-(4-cyclopropyl-phenyl)-1-oxo-2,8-diaza-spiro[4.5]dec-8-yl]-propionamide;
N-Butyl-2-[2-(4-cyclopropyl-phenyl)-1-oxo-2,8-diaza-spiro[4.5]dec-8-yl]-butyramide;
N-Butyl-2-[2-(4-cyclopropyl-phenyl)-1-oxo-2,8-diaza-spiro[4.5]dec-8-yl]-2-phenyl-acetamide;
2-[2-(4-Cyclopropyl-phenyl)-1-oxo-2,8-diaza-spiro[4.5]dec-8-yl]-hexanoic acid butylamide;
N-Butyl-2-[2-(4-cyclopropyl-phenyl)-1-oxo-2,8-diaza-spiro[4.5]dec-8-yl]-3-methyl-butyramide;
2-(4-Cyclopropyl-phenyl)-8-((S)-2-hydroxy-2-phenyl-ethyl)-2,8-diaza-spiro[4.5]decan-1-one;
2-(4-Cyclopropyl-phenyl)-8-((R)-2-hydroxy-2-phenyl-ethyl)-2,8-diaza-spiro[4.5]decan-1-one;
2-(4-Cyclopropyl-phenyl)-8-(2-hydroxy-2-phenyl-propyl)-2,8-diaza-spiro[4.5]decan-1-one;
2-(4-Cyclopropyl-phenyl)-8-[(R)-2-(4-fluoro-phenyl)-2-hydroxy-ethyl]-2,8-diaza-spiro[4.5]decan-1-one;
8-[(R)-2-(3-Chloro-phenyl)-2-hydroxy-ethyl]-2-(4-cyclopropyl-phenyl)-2,8-diaza-spiro[4.5]decan-1-one;
2-(4-Cyclopropyl-phenyl)-8-[2-(3,4-dichloro-phenyl)-2-hydroxy-ethyl]-2,8-diaza-spiro[4.5]decan-1-one; and
2-(4-Cyclopropyl-phenyl)-8-[2-(2,4-dichloro-phenyl)-2-hydroxy-ethyl]-2,8-diaza-spiro[4.5]decan-1-one.
Examples of an also preferred compound according to formula (I) as described above is selected from the group consisting of:
8-[2-(2-Chloro-6-fluoro-phenyl)-2-hydroxy-ethyl]-2-(4-cyclopropyl-phenyl)-2,8-diaza-spiro[4.5]decan-1-one;
3-[2-(4-Cyclopropyl-phenyl)-1-oxo-2,8-diaza-spiro[4.5]dec-8-yl]-2-hydroxy-3-(4-methoxy-phenyl)-propionamide;
(S)-2-[2-(4-Cyclopropyl-phenyl)-1-oxo-2,8-diaza-spiro[4.5]dec-8-yl]-hexanoic acid butylamide;
(R)-2-[2-(4-Cyclopropyl-phenyl)-1-oxo-2,8-diaza-spiro[4.5]dec-8-yl]-hexanoic acid butylamide;
8-[2-(2,4-Dichloro-phenyl)-2-oxo-ethyl]-2-(4-ethyl-phenyl)-2,8-diaza-spiro[4.5]decan-1-one;
8-[2-(2,4-Dichloro-phenyl)-2-hydroxy-ethyl]-2-[4-(2,2,2-trifluoro-ethoxy)-phenyl]-2,8-diaza-spiro[4.5]decan-1-one;
8-[2-(2,4-Dichloro-phenyl)-2-hydroxy-ethyl]-2-[6-((R)-2,2,2-trifluoro-1-methyl-ethoxy)-pyridin-3-yl]-2,8-diaza-spiro[4.5]decan-1-one;
8-[2-(2,4-Dichloro-phenyl)-2-hydroxy-ethyl]-2-[4-(2,2,2-trifluoro-ethyl)-phenyl]-2,8-diaza-spiro[4.5]decan-1-one;
8-[2-(2-Chloro-6-fluoro-phenyl)-2-hydroxy-ethyl]-2-[4-(2,2,2-trifluoro-ethoxy)-phenyl]-2,8-diaza-spiro[4.5]decan-1-one;
8-[2-(2-Chloro-6-fluoro-phenyl)-2-hydroxy-ethyl]-2-[4-((R)-2,2,2-trifluoro-1-methyl-ethoxy)-phenyl]-2,8-diaza-spiro[4.5]decan-1-one;
8-[2-(2-Chloro-6-fluoro-phenyl)-2-hydroxy-ethyl]-2-[6-((R)-2,2,2-trifluoro-1-methyl-ethoxy)-pyridin-3-yl]-2,8-diaza-spiro[4.5]decan-1-one;
8-[2-(2-Chloro-6-fluoro-phenyl)-2-hydroxy-ethyl]-2-[4-(2,2,2-trifluoro-ethyl)-phenyl]-2,8-diaza-spiro[4.5]decan-1-one;
8-[2-(2,4-Dichloro-phenyl)-2-hydroxy-ethyl]-2-[4-((R)-2,2,2-trifluoro-1-methyl-ethoxy)-phenyl]-2,8-diaza-spiro[4.5]decan-1-one;
8-[2-(2,4-Dichloro-phenyl)-2-hydroxy-ethyl]-2-[4-((S)-2,2,2-trifluoro-1-methyl-ethoxy)-phenyl]-2,8-diaza-spiro[4.5]decan-1-one;
8-[2-(2,4-Dichloro-phenyl)-2-hydroxy-ethyl]-2-[6-((S)-2,2,2-trifluoro-1-methyl-ethoxy)-pyridin-3-yl]-2,8-diaza-spiro[4.5]decan-1-one;
8-[2-(2-Chloro-6-fluoro-phenyl)-2-hydroxy-ethyl]-2-[4-((S)-2,2,2-trifluoro-1-methyl-ethoxy)-phenyl]-2,8-diaza-spiro[4.5]decan-1-one; and
8-[2-(2-Chloro-6-fluoro-phenyl)-2-hydroxy-ethyl]-2-[6-((S)-2,2,2-trifluoro-1-methyl-ethoxy)-pyridin-3-yl]-2,8-diaza-spiro[4.5]decan-1-one.
A further preferred example of a compound according to formula (I) as described above is selected from the group consisting of:
2-(4-Cyclopropyl-phenyl)-8-(1-phenyl-propyl)-2,8-diaza-spiro[4.5]decan-1-one;
N-Butyl-2-[2-(4-cyclopropyl-phenyl)-1-oxo-2,8-diaza-spiro[4.5]dec-8-yl]-acetamide;
2-[2-(4-Cyclopropyl-phenyl)-1-oxo-2,8-diaza-spiro[4.5]dec-8-yl]-N-(4-trifluoromethyl-benzyl)-acetamide;
2-[2-(4-Cyclopropyl-phenyl)-1-oxo-2,8-diaza-spiro[4.5]dec-8-yl]-N-(4-fluoro-phenyl)-acetamide;
3-[2-(4-Cyclopropyl-phenyl)-1-oxo-2,8-diaza-spiro[4.5]dec-8-yl]-N-(4-trifluoromethyl-benzyl)-propionamide;
3-[2-(4-Cyclopropyl-phenyl)-1-oxo-2,8-diaza-spiro[4.5]dec-8-yl]-N-(4-fluoro-phenyl)-propionamide;
2-(4-Cyclopropyl-phenyl)-8-(2-hydroxy-2-phenyl-ethyl)-2,8-diaza-spiro[4.5]decan-1-one;
8-[2-(4-Chloro-phenyl)-2-hydroxy-ethyl]-2-(4-cyclopropyl-phenyl)-2,8-diaza-spiro[4.5]decan-1-one;
2-[2-(4-Cyclopropyl-phenyl)-1-oxo-2,8-diaza-spiro[4.5]dec-8-yl]-N-(4-fluoro-phenyl)-propionamide;
2-[2-(4-Cyclopropyl-phenyl)-1-oxo-2,8-diaza-spiro[4.5]dec-8-yl]-hexanoic acid butylamide;
N-Butyl-2-[2-(4-cyclopropyl-phenyl)-1-oxo-2,8-diaza-spiro[4.5]dec-8-yl]-3-methyl-butyramide;
2-(4-Cyclopropyl-phenyl)-8-((R)-2-hydroxy-2-phenyl-ethyl)-2,8-diaza-spiro[4.5]decan-1-one; and
2-(4-Cyclopropyl-phenyl)-8-[(R)-2-(4-fluoro-phenyl)-2-hydroxy-ethyl]-2,8-diaza-spiro[4.5]decan-1-one.
Also further preferred example of a compound according to formula (I) as described above is selected from the group consisting of:
(R)-2-[2-(4-Cyclopropyl-phenyl)-1-oxo-2,8-diaza-spiro[4.5]dec-8-yl]-hexanoic acid butylamide;

8-[2-(2,4-Dichloro-phenyl)-2-hydroxy-ethyl]-2-[4-(2,2,2-trifluoro-ethyl)-phenyl]-2,8-diaza-spiro[4.5]decan-1-one; and 8-[2-(2,4-Dichloro-phenyl)-2-hydroxy-ethyl]-2-[4-((S)-2,2,2-trifluoro-1-methyl-ethoxy)-phenyl]-2,8-diaza-spiro[4.5]decan-1-one.

Processes for the manufacture of compounds of formula (I) are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Compounds of formula (I), wherein $R^3$ is —$R^4$ are readily accessible as outlined in Scheme 1 by reductive amination. Compounds of general formula (II) are reacted with compounds of general formula (III) in the presence of a reducing agent such as sodium triacetoxyborohydride, sodium borohydride or sodium cyanoborohydride in a solvent such as e.g. THF, methanol or ethanol in the presence or not of acetic acid to give compounds of formula (I), wherein $R^3$ is —$R^4$.

Scheme 1

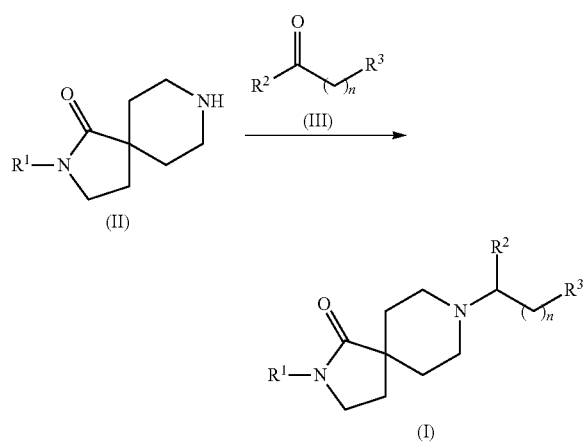

Compounds of formula (I), wherein $R^3$ is —C(OH)$R^5R^6$ and n is zero are readily accessible as outlined in Scheme 2.

Compounds of general formula (II) are reacted with compounds of general formula (IV) in the presence of a base such as e.g. triethylamine in a solvent such as e.g. dichloromethane to give compounds of formula (I), wherein $R^3$ is —C(OH)$R^5R^6$ and n is zero.

Scheme 2

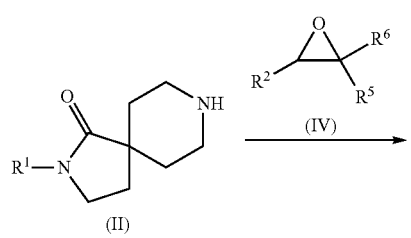

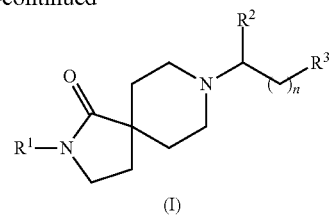

Compounds of formula (I), wherein $R^3$ is —C(O)$NR^7R^8$ are readily accessible in a stepwise process as outlined in Scheme 3.

Compounds of general formula (II) are reacted with compounds of general formula (V) in the presence of a base such as e.g. triethylamine in a solvent such as e.g. dichloromethane (step a)) to give compounds of general formula (VI).

Compounds of general formula (VI) are reacted with compounds of general formula (VII) in the presence of a coupling reagent such as N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a solvent e.g. N,N-dimethylformamide (DMF) or dioxane, in the presence or not of a base such as triethylamine, diisopropylethylamine or 4-(dimethylamino)pyridine (step b)) to give compounds of formula (I), wherein $R^3$ is —C(O)$NR^7R^8$.

Scheme 3

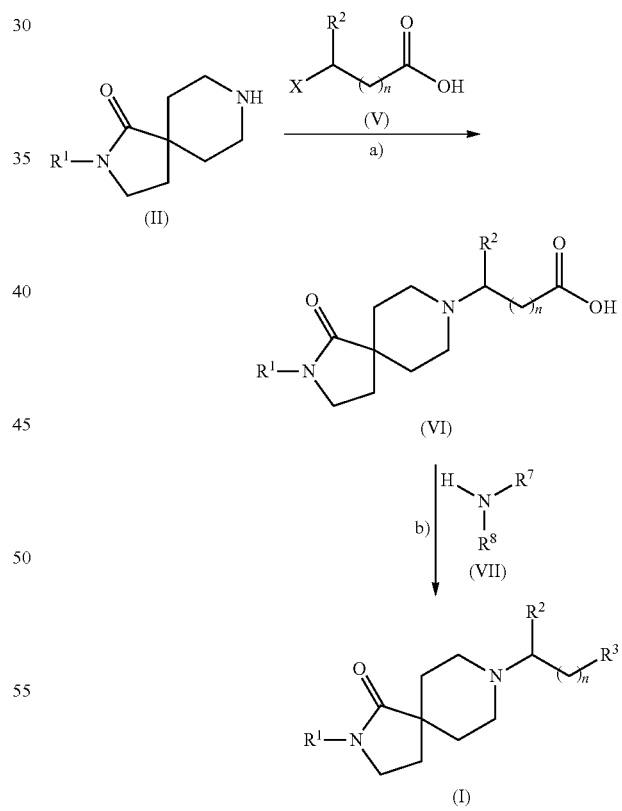

X is halogen e.g. chlorine or bromine

Compounds of formula (II) are readily accessible in a stepwise process as outlined in Scheme 4.

Compounds of general formula (VIII) can be alkylated at the appropriate position by treatment with a suitable base such as e.g. lithium diisopropylamide or butyl lithium in an appropriate solvent such as THF, DMF, diethylether, followed by addition of the appropriate electrophile such as e.g. 1-bromo-2-methoxyethane or 1-chloro-2-methoxyethane to give compounds of general formula (IX) (step c)).

Compounds of formula (IX) are subsequently reacted with derivatives of general formula (X) in the presence of an organoaluminium reagent such as e.g. dimethylaluminium chloride or trimethylaluminium in a solvent such as toluene or dioxane to give the spirocyclic compounds of general formula (XI) (step d)).

The protecting group (PG) of compounds of general formula (XI) can then be removed by standard conditions e.g. hydrogenation or reaction with an acid, preferably HCl or TFA, to give the compounds of general formula (II) (step e)).

Scheme 4

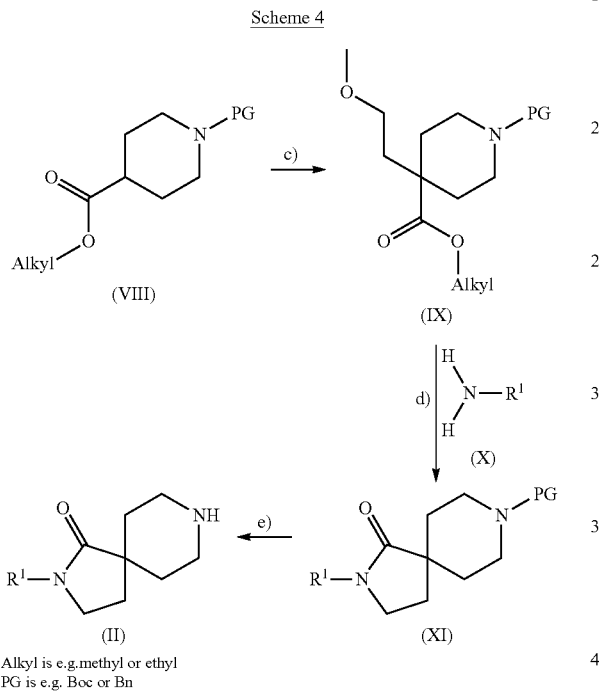

Alkyl is e.g. methyl or ethyl
PG is e.g. Boc or Bn

Compounds of formula (I) are also readily accessible in a one step process as outlined in Scheme 5.

Scheme 5

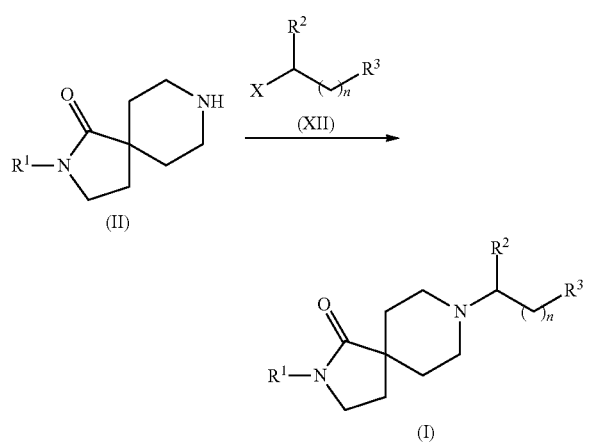

X is halogen e.g. chlorine or bromine

Compounds of general formula (II) are reacted with compounds of general formula (XII) in the presence of a base such as e.g. triethylamine in a solvent such as e.g. dichloromethane to give compounds of general formula (I).

Preferred is a process for the preparation of a compound according to formula (I) as described above comprising a) the reaction of a compound of formula (II) in the presence of a compound of formula (III);

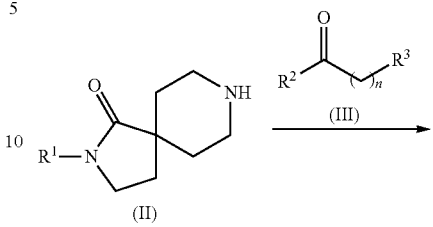

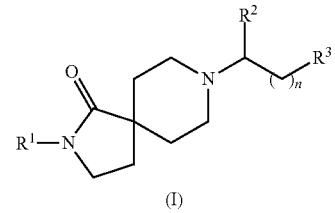

Preferably in the presence of a reducing agent, particularly sodium triacetoxyborohydride, in a solvent, particularly THF, in the presence or not of an acid, particularly in the presence of acetic acid, and at a temperature between −20° C. and reflux of solvent, particularly at room temperature, wherein $R^1$, $R^2$ and n are as defined above and $R^3$ is —$R^4$;

b) the reaction of a compound of formula (II) in the presence of a compound of formula (IV);

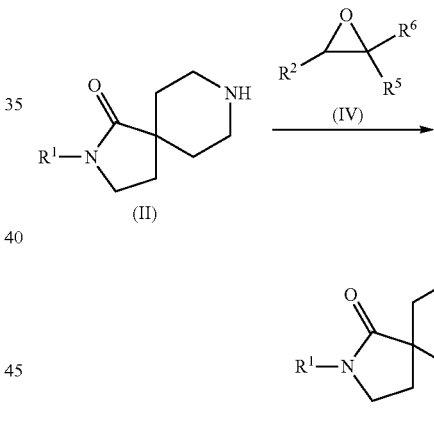

Preferably in the presence of a base, particularly triethylamine, in a solvent, particularly dichloromethane, and at a temperature between 0° C. and reflux of solvent, particularly at reflux of solvent, wherein $R^1$, $R^2$, $R^5$ and $R^6$ are as defined above, $R^3$ is —$C(OH)R^5R^6$ and n is zero;

or c) the reaction of a compound of formula (VI) in the presence of a compound of formula (VII);

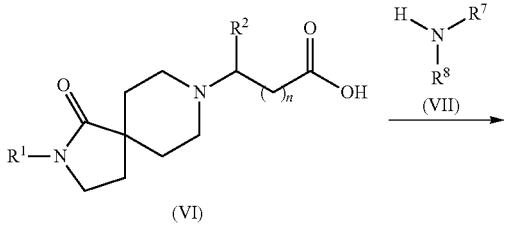

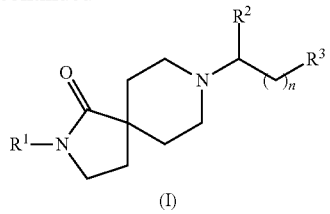

(I)

Preferably in the presence of a coupling agent, particularly TBTU, in the presence or not of a base, particularly in the presence of triethylamine, in a solvent, particularly DMF, and at a temperature between −20° C. and reflux of solvent, particularly at room temperature, wherein $R^1$, $R^2$, $R^7$, $R^8$ and n are as defined above and $R^3$ is —C(O)N$R^7R^8$.

Preferred intermediates are selected from 4-(2-Methoxy-ethyl)-piperidine-1,4-dicarboxylic acid 1-tert-butyl ester 4-ethyl ester;

2-(4-Cyclopropyl-phenyl)-2,8-diaza-spiro[4.5]decan-1-one;

2-(2-Chloro-4-cyclopropyl-phenyl)-2,8-diaza-spiro[4.5]decan-1-one;

1-Benzyl-4-(2-methoxy-ethyl)-piperidine-4-carboxylic acid ethyl ester;

[2-(4-Cyclopropyl-phenyl)-1-oxo-2,8-diaza-spiro[4.5]dec-8-yl]-acetic acid;

3-[2-(4-Cyclopropyl-phenyl)-1-oxo-2,8-diaza-spiro[4.5]dec-8-yl]-propionic acid;

2-[2-(4-Cyclopropyl-phenyl)-1-oxo-2,8-diaza-spiro[4.5]dec-8-yl]-propionic acid;

2-[2-(4-Cyclopropyl-phenyl)-1-oxo-2,8-diaza-spiro[4.5]dec-8-yl]-butyric acid;

[2-(4-Cyclopropyl-phenyl)-1-oxo-2,8-diaza-spiro[4.5]dec-8-yl]-phenyl-acetic acid;

2-[2-(4-Cyclopropyl-phenyl)-1-oxo-2,8-diaza-spiro[4.5]dec-8-yl]-hexanoic acid; and 2-[2-(4-Cyclopropyl-phenyl)-1-oxo-2,8-diaza-spiro[4.5]dec-8-yl]-3-methyl-butyric acid.

A further object of the present invention comprises a compound according to formula (I) as described above, when manufactured according to any one of the described processes.

A further object of the invention is a compound according to formula (I) as described above for use as therapeutically active substance.

Likewise an object of the present invention is a pharmaceutical composition comprising a compound according to formula (I) as described above and a therapeutically inert carrier.

A further object of the invention is the use of a compound according to formula (I) as described above for the treatment or prophylaxis of diabetes, metabolic syndrome, dyslipidemia, atherosclerosis or obesity.

Also preferred is the use of a compound according to formula (I) as described above for the treatment or prophylaxis of cardiovascular diseases, myocardial dysfunction or inflammation.

Particularly preferred is the use of a compound according to formula (I) as described above for the treatment or prophylaxis of diabetes.

Moreover preferred is the use of a compound according to formula (I) as described above for the treatment or prophylaxis of diabetes Type II.

A further preferred embodiment of the present invention is the use of a compound according to formula (I) as described above for the preparation of a medicament for the treatment or prophylaxis of diabetes, metabolic syndrome, dyslipidemia, atherosclerosis or obesity.

Also further preferred is the use of a compound according to formula (I) as described above for the preparation of a medicament for the treatment or prophylaxis of cardiovascular diseases, myocardial dysfunction or inflammation.

Particularly preferred is the use of a compound according to formula (I) as described above for the preparation of a medicament for the treatment or prophylaxis of diabetes.

Moreover preferred is the use of a compound according to formula (I) as described above for the preparation of a medicament for the treatment or prophylaxis of diabetes Type II.

Also an object of the present invention is a compound according to formula (I) as described above for the treatment or prophylaxis of illnesses which are caused by disorders associated e.g. with the enzyme hormone-sensitive lipase.

Further preferred is a compound according to formula (I) as described above for the treatment or prophylaxis of diabetes, metabolic syndrome, dyslipidemia, atherosclerosis or obesity.

Also further preferred is a compound according to formula (I) as described above for the treatment or prophylaxis of cardiovascular diseases, myocardial dysfunction or inflammation.

Particularly preferred is a compound according to formula (I) as described above for the treatment or prophylaxis of diabetes.

Moreover preferred is a compound according to formula (I) as described above for the treatment or prophylaxis of diabetes Type II.

Also an object of the invention is a method for the treatment or prophylaxis of diabetes, metabolic syndrome, dyslipidemia, atherosclerosis or obesity, which method comprises administering an effective amount of a compound according to formula (I) as described above.

Also preferred is a method for the treatment or prophylaxis of cardiovascular diseases, myocardial dysfunction or inflammation, which method comprises administering an effective amount of a compound according to formula (I) as described above.

Particularly preferred is a method for the treatment or prophylaxis of diabetes, which method comprises administering an effective amount of a compound according to formula (I) as described above.

Moreover preferred is a method for the treatment or prophylaxis of diabetes Type II, which method comprises administering an effective amount of a compound according to formula (I) as described above.

Also an embodiment of the present invention is the use of a compound according to formula (I) as described above for the treatment or prophylaxis nonalkoholic fatty liver disease or nonalkoholic steatohepatitis.

Also an embodiment of the present invention is the use of a compound according to formula (I) as described above for the preparation of a medicament for the treatment or prophylaxis of nonalkoholic fatty liver disease or nonalkoholic steatohepatitis.

Also a particular embodiment of the present invention is a compound according to formula (I) as described above for the treatment or prophylaxis of nonalkoholic fatty liver disease or nonalkoholic steatohepatitis.

Also an embodiment of the present invention is a method for the treatment or prophylaxis of nonalkoholic fatty liver disease or nonalkoholic steatohepatitis, which method comprises administering an effective amount of a compound according to formula (I) as described above.

With respect to inhibition of HSL, compounds as described above have $IC_{50}$ values between 0.005 uM and 1000 uM, preferred compounds have $IC_{50}$ values between 0.01 uM and 10 uM, particularly preferred compounds have $IC_{50}$ values between 0.01 uM and 0.5 uM.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula (I) and their pharmaceutically acceptable salts can be used for the prophylaxis or treatment of diabetes, metabolic syndrome, dyslipidemia, atherosclerosis and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

2-(4-Cyclopropyl-phenyl)-8-(3-phenyl-propyl)-2,8-diaza-spiro[4.5]decan-1-one

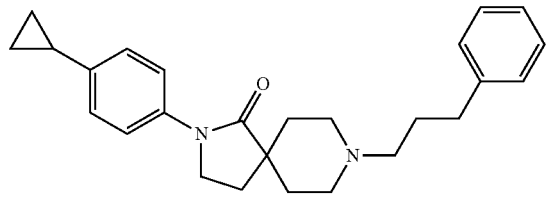 [SMILES: O=C1N(c2ccc(C3CC3)cc2)CCC12CCN(CCCc1ccccc1)CC2]

Step 1

4-(2-Methoxy-ethyl)-piperidine-1,4-dicarboxylic acid 1-tert-butyl ester 4-ethyl ester

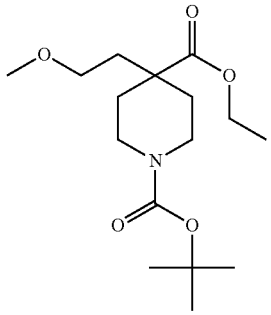 [SMILES: CCOC(=O)C1(CCOC)CCN(C(=O)OC(C)(C)C)CC1]

To a solution of 38 mL (76 mmol) LDA in THF (2N) was added 9.8 g (38 mmol) 1-tert-butyl 4-ethyl piperidine-1,4-dicarboxylate (commercially available) in 10 mL THF at −5° C. and stirred at −5° C. for 3 h. 10.58 g (76 mmol) 1-bromo-2-methoxyethane in 10 mL THF was added drop-wise, stirred for 1 h at −5° C. and stirred at room temperature over night. KHSO$_4$ aq. (1M) was added and the mixture was extracted with ethyl acetate. The combined organic layers were dried with MgSO$_4$ and evaporated to dryness. The residue was purified by column chromatography on silica eluting with a gradient formed from ethyl acetate and heptane to yield after evaporation of the product containing fractions 8.19 g (68%) of the title compound as yellow oil. MS m/e: 315.2 [M+H]$^+$.

Step 2

2-(4-Cyclopropyl-phenyl)-2,8-diaza-spiro[4.5]decan-1-one

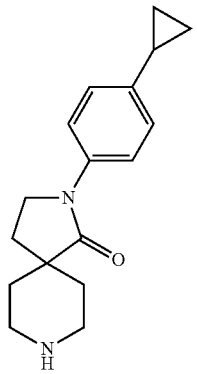 [SMILES: O=C1N(c2ccc(C3CC3)cc2)CCC12CCNCC2]

A mixture of 1.3 g (4.1 mmol) 4-(2-Methoxy-ethyl)-piperidine-1,4-dicarboxylic acid 1-tert-butyl ester 4-ethyl ester, 0.604 g (4.5 mmol) 4-cyclopropylaniline and 8.24 mL (8.24 mmol) dimethylaluminum chloride (1N in hexane) in 100 mL toluene was stirred at 115° C. for 15 h. After cooling to room temperature the mixture was poured into ice, the mixture was acidified with HCl aq. to pH=2 and extracted with ethyl acetate. The aqueous layer was basified with NaOH pellets to pH=8 and extracted with DCM. The combined organic layers were dried with MgSO$_4$ and evaporated to dryness. The residue was purified by column chromatography on silica (amine) with a gradient formed from ethyl acetate and methanol to yield after evaporation of the product containing fractions 0.468 g (42%) of the title compound as light yellow solid. MS m/e: 270.0 [M+H]+.

Step 3

2-(4-Cyclopropyl-phenyl)-8-(3-phenyl-propyl)-2,8-diaza-spiro[4.5]decan-1-one

A mixture of 20 mg (0.074 mmol) 2-(4-Cyclopropyl-phenyl)-2,8-diaza-spiro[4.5]decan-1-one, 42 uL acetic acid, 44 mg (0.148 mmol) sodium triacetyoxyborohydride and excess 3-phenyl-propionaldehyde in 2 mL THF was stirred for at room temperature over night. Water was added, the mixture was extracted with ethyl acetate and the combined organic layers were evaporated to dryness. The residue was taken up in methanol and subjected to purification by preparative HPLC on reversed phase eluting with a gradient formed from acetonitrile, water and NEt3. The product containing fractions were evaporated to yield 7.1 mg (25%) of the title compound. MS m/e: 389.4 [M+H]+.

Example 2

2-(4-Cyclopropyl-phenyl)-8-phenethyl-2,8-diaza-spiro[4.5]decan-1-one

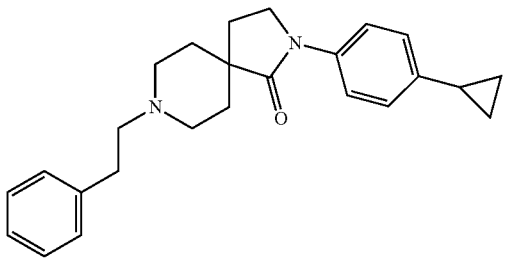 [SMILES: O=C1N(c2ccc(C3CC3)cc2)CCC12CCN(CCc1ccccc1)CC2]

In analogy to the procedure described for the synthesis of 2-(4-Cyclopropyl-phenyl)-8-(3-phenyl-propyl)-2,8-diaza-spiro[4.5]decan-1-one (example 1) the title compound was prepared from 2-(4-Cyclopropyl-phenyl)-2,8-diaza-spiro[4.5]decan-1-one and phenyl-acetaldehyde (commercially available) through reductive amination. MS m/e: 375.4 [M+H]+.

Example 3

2-(4-Cyclopropyl-phenyl)-8-(4-trifluoromethyl-benzyl)-2,8-diaza-spiro[4.5]decan-1-one

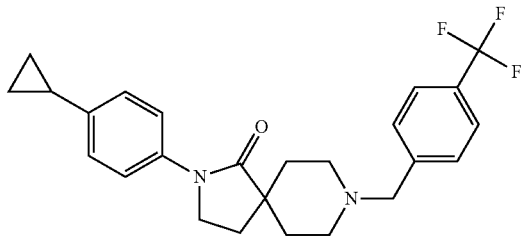 [SMILES: O=C1N(c2ccc(C3CC3)cc2)CCC12CCN(Cc1ccc(C(F)(F)F)cc1)CC2]

In analogy to the procedure described for the synthesis of 2-(4-Cyclopropyl-phenyl)-8-(3-phenyl-propyl)-2,8-diaza-spiro[4.5]decan-1-one (example 1) the title compound was prepared from 2-(4-Cyclopropyl-phenyl)-2,8-diaza-spiro[4.5]decan-1-one and 4-trifluoromethyl-benzaldehyde (commercially available) through reductive amination. MS m/e: 429.4 [M+H]+.

Example 4

2-(4-Cyclopropyl-phenyl)-8-(1-phenyl-ethyl)-2,8-diaza-spiro[4.5]decan-1-one

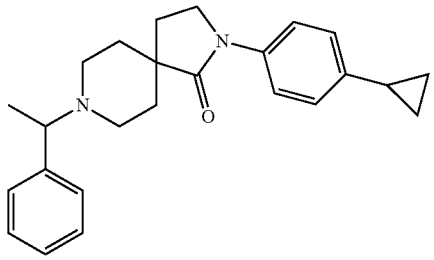 [SMILES: CC(c1ccccc1)N1CCC2(CCN(c3ccc(C4CC4)cc3)C2=O)CC1]

In analogy to the procedure described for the synthesis of 2-(4-Cyclopropyl-phenyl)-8-(3-phenyl-propyl)-2,8-diaza-spiro[4.5]decan-1-one (example 1) the title compound was prepared from 2-(4-Cyclopropyl-phenyl)-2,8-diaza-spiro[4.5]decan-1-one and 1-phenyl-ethanone (commercially available) through reductive amination. MS m/e: 375.3 [M+H]+.

Example 5

2-(4-Cyclopropyl-phenyl)-8-[1-(3-trifluoromethyl-phenyl)-ethyl]-2,8-diaza-spiro[4.5]decan-1-one

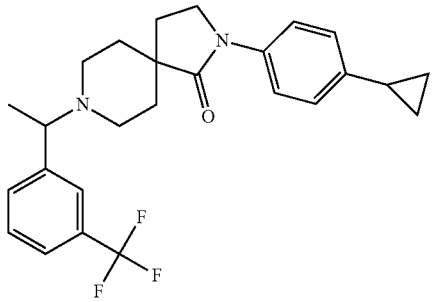 [SMILES: CC(c1cccc(C(F)(F)F)c1)N1CCC2(CCN(c3ccc(C4CC4)cc3)C2=O)CC1]

In analogy to the procedure described for the synthesis of 2-(4-Cyclopropyl-phenyl)-8-(3-phenyl-propyl)-2,8-diaza-spiro[4.5]decan-1-one (example 1) the title compound was prepared from 2-(4-Cyclopropyl-phenyl)-2,8-diaza-spiro[4.5]decan-1-one and 1-(3-trifluoromethyl-phenyl)-ethanone (commercially available) through reductive amination. MS m/e: 443.4 [M+H]+.

Example 6

2-(2-Chloro-4-cyclopropyl-phenyl)-8-(1-phenyl-ethyl)-2,8-diaza-spiro[4.5]decan-1-one

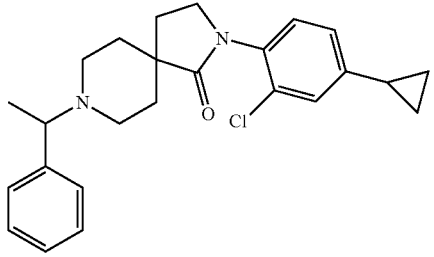 [SMILES: CC(c1ccccc1)N1CCC2(CCN(c3ccc(C4CC4)cc3Cl)C2=O)CC1]

Step 1

2-(2-Chloro-4-cyclopropyl-phenyl)-2,8-diaza-spiro[4.5]decan-1-one

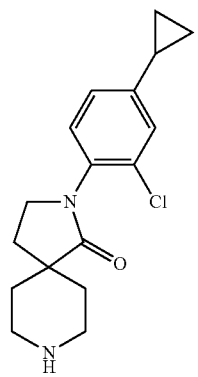 [SMILES: O=C1N(c2ccc(C3CC3)cc2Cl)CCC12CCNCC2]

A mixture of 0.275 g (1 mmol) 2-(4-Cyclopropyl-phenyl)-2,8-diaza-spiro[4.5]decan-1-one. 1.57 g (11.3 mmol) sulfuryl chloride and 0.154 g (1.52 mmol) NEt$_3$ in 50 mL CHCl$_3$ was stirred at room temperature. After evaporation of the volatiles the residue was taken up in DMF and subjected to purification by preparative HPLC on reversed phase eluting with a gradient formed from acetonitrile, water and NEt$_3$. The product containing fractions were evaporated to yield 94 mg (30%) of the title compound as light yellow gum. MS m/e: 305.1 [M+H]$^+$.

Step 2

2-(2-Chloro-4-cyclopropyl-phenyl)-8-(1-phenyl-ethyl)-2,8-diaza-spiro[4.5]decan-1-one In analogy to the procedure described for the synthesis of 2-(4-Cyclopropyl-phenyl)-8-(3-phenyl-propyl)-2,8-diaza-spiro[4.5]decan-1-one (example 1) the title compound was prepared from 2-(2-Chloro-4-cyclopropyl-phenyl)-2,8-diaza-spiro[4.5]decan-1-one and 1-phenyl-ethanone (commercially available) through reductive amination. MS m/e: 409.4 [M+H]$^+$.

Example 7

2-(4-Cyclopropyl-phenyl)-8-(1-phenyl-propyl)-2,8-diaza-spiro[4.5]decan-1-one

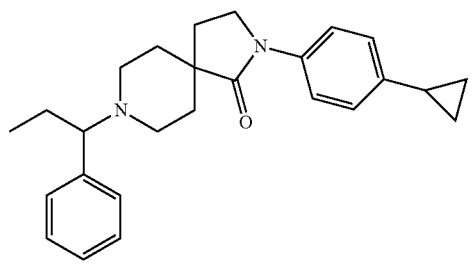 [SMILES: CCC(c1ccccc1)N1CCC2(CCN(c3ccc(C4CC4)cc3)C2=O)CC1]

In analogy to the procedure described for the synthesis of 2-(4-Cyclopropyl-phenyl)-8-(3-phenyl-propyl)-2,8-diaza-spiro[4.5]decan-1-one (example 1) the title compound was prepared from 2-(4-Cyclopropyl-phenyl)-2,8-diaza-spiro[4.5]decan-1-one and 1-phenyl-propan-1-one (commercially available) through reductive amination. MS m/e: 389.4 [M+H]$^+$.

Example 8

8-Benzyl-2-(4-trifluoromethoxy-phenyl)-2,8-diaza-spiro[4.5]decan-1-one

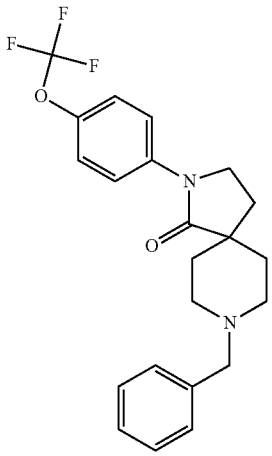 [SMILES: O=C1N(c2ccc(OC(F)(F)F)cc2)CCC12CCN(Cc1ccccc1)CC2]

Step 1

1-Benzyl-4-(2-methoxy-ethyl)-piperidine-4-carboxylic acid ethyl ester

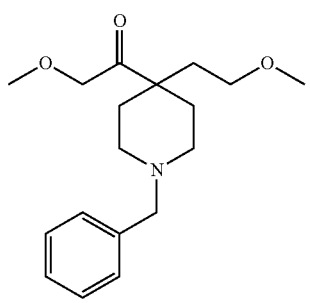

In analogy to the procedure described for the synthesis of 4-(2-Methoxy-ethyl)-piperidine-1,4-dicarboxylic acid 1-tert-butyl ester 4-ethyl ester (example 1, step 1) the title compound was prepared from 1-benzyl-piperidine-4-carboxylic acid ethyl ester and 1-bromo-2-methoxy-ethane with deprotonation with LDA. MS m/e: 306.2 [M+H]$^+$.

Step 2

8-Benzyl-2-(4-trifluoromethoxy-phenyl)-2,8-diaza-spiro[4.5]decan-1-one

In analogy to the procedure described for the synthesis of 2-(4-Cyclopropyl-phenyl)-2,8-diaza-spiro[4.5]decan-1-one (example 1, step 2) the title compound was prepared from 1-benzyl-4-(2-methoxy-ethyl)-piperidine-4-carboxylic acid ethyl ester and 4-trifluoromethoxy-phenylamine in the presence of dimethylaluminium chloride. MS m/e: 405.4 [M+H]+.

Example 9

2-[2-(4-Cyclopropyl-phenyl)-1-oxo-2,8-diaza-spiro[4.5]dec-8-yl]-N-ethyl-acetamide

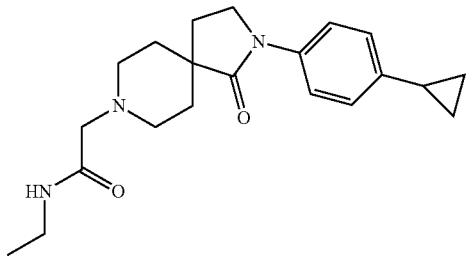 [SMILES: CCNC(=O)CN1CCC2(CC1)CCN(c1ccc(C3CC3)cc1)C2=O]

Step 1

[2-(4-Cyclopropyl-phenyl)-1-oxo-2,8-diaza-spiro[4.5]dec-8-yl]-acetic acid

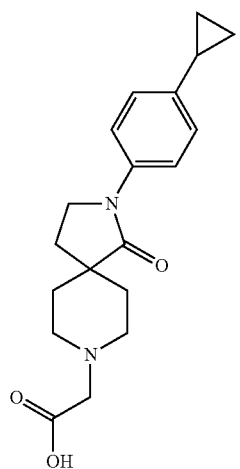 [SMILES: O=C(O)CN1CCC2(CC1)CCN(c1ccc(C3CC3)cc1)C2=O]

A mixture of 0.4 g (1.47 mmol) 2-(4-Cyclopropyl-phenyl)-2,8-diaza-spiro[4.5]decan-1-one, 0.226 g (1.63 mmol) bromoacetic acid and 0.299 g (2.96 mmol) NEt$_3$ in 50 mL DCM was stirred at room temperature for 16 h. The mixture was concentrated and used without further purification in the consecutive step. MS m/e: 329.3 [M+H]+.

Step 2

2-[2-(4-Cyclopropyl-phenyl)-1-oxo-2,8-diaza-spiro[4.5]dec-8-yl]-N-ethyl-acetamide A mixture of mg 42.7 mg (0.13 mmol) [2-(4-Cyclopropyl-phenyl)-1-oxo-2,8-diaza-spiro[4.5]dec-8-yl]-acetic acid, 54.2 mg (0.195 mmol) TBTU, 26 mg (0.26 mmol) NEt$_3$ and 8.7 mg (0.195 mmol) ethylamine in 2 mL DMF was stirred at room temperature for 16 h and evaporated to dryness. The residue was taken up in DMF and subjected to purification by preparative HPLC on reversed phase eluting with a gradient formed from acetonitrile, water and NEt$_3$. The product containing fractions were evaporated to yield 16.2 mg (35%) of the title compound. MS m/e: 356.3 [M+H]+.

Example 10

2-[2-(4-Cyclopropyl-phenyl)-1-oxo-2,8-diaza-spiro[4.5]dec-8-yl]-N,N-diethyl-acetamide

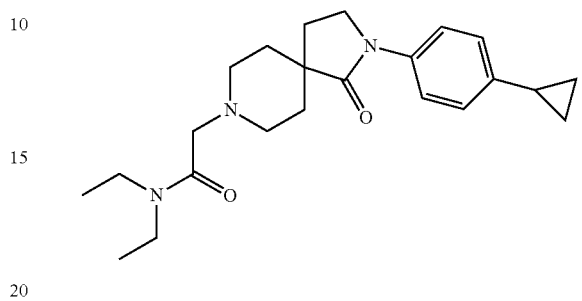

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and diethylamine. MS m/e: 384.4 [M+H]+.

Example 11

N-Butyl-2-[2-(4-cyclopropyl-phenyl)-1-oxo-2,8-diaza-spiro[4.5]dec-8-yl]-acetamide

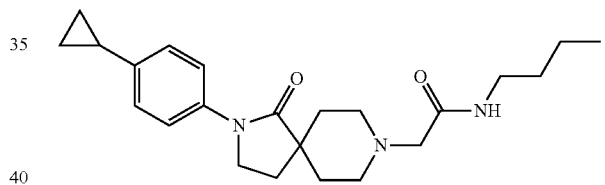

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and butylamine. MS m/e: 384.4 [M+H]+.

Example 12

2-[2-(4-Cyclopropyl-phenyl)-1-oxo-2,8-diaza-spiro[4.5]dec-8-yl]-N-(4-trifluoromethyl-benzyl)-acetamide

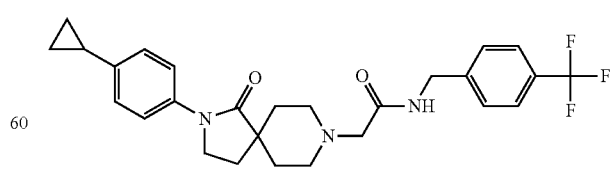

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8- diaza-spiro[4.5]dec-8-yl]-acetic acid and 4-trifluoromethyl-benzylamine. MS m/e: 486.4 [M+H]⁺.

Example 13

2-[2-(4-Cyclopropyl-phenyl)-1-oxo-2,8-diaza-spiro[4.5]dec-8-yl]-N-(4-fluoro-phenyl)-acetamide

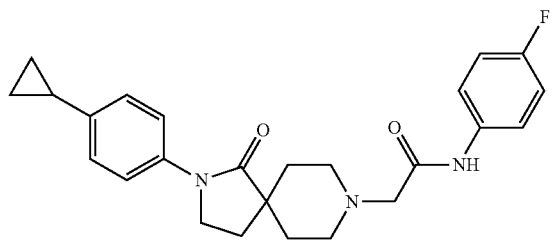 [SMILES: O=C(CN1CCC2(CC1)CCN(c1ccc(C3CC3)cc1)C2=O)Nc1ccc(F)cc1]

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and 4-fluoro-phenylamine. MS m/e: 422.3 [M+H]⁺.

Example 14

2-(4-Cyclopropyl-phenyl)-8-(2-oxo-2-pyrrolidin-1-yl-ethyl)-2,8-diaza-spiro[4.5]decan-1-one

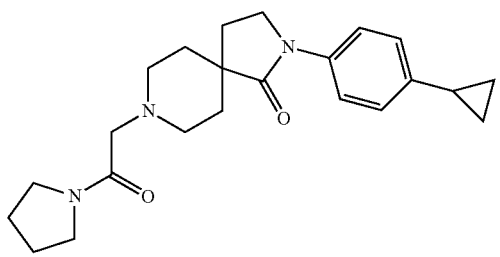 [SMILES: O=C(CN1CCC2(CC1)CCN(c1ccc(C3CC3)cc1)C2=O)N1CCCC1]

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and pyrrolidine. MS m/e: 382.3 [M+H]⁺.

Example 15

N-Benzyl-2-[2-(4-cyclopropyl-phenyl)-1-oxo-2,8-diaza-spiro[4.5]dec-8-yl]-N-methyl-acetamide

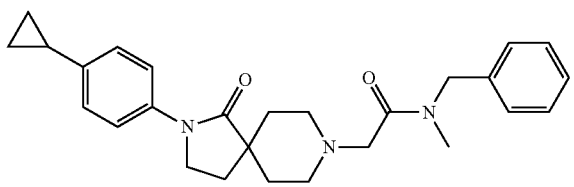 [SMILES: CN(Cc1ccccc1)C(=O)CN1CCC2(CC1)CCN(c1ccc(C3CC3)cc1)C2=O]

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and benzyl-methyl-amine. MS m/e: 432.4 [M+H]⁺.

Example 16

N-Cyclohexyl-2-[2-(4-cyclopropyl-phenyl)-1-oxo-2,8-diaza-spiro[4.5]dec-8-yl]-N-methyl-acetamide

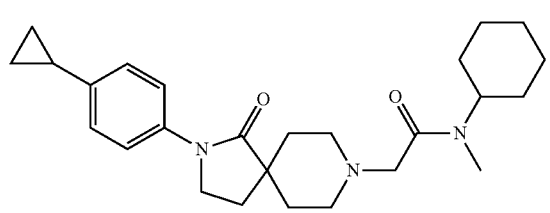 [SMILES: CN(C(=O)CN1CCC2(CC1)CCN(c1ccc(C3CC3)cc1)C2=O)C1CCCCC1]

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and cyclohexyl-methyl-amine. MS m/e: 424.4 [M+H]⁺.

Example 17

2-[2-(4-Cyclopropyl-phenyl)-1-oxo-2,8-diaza-spiro[4.5]dec-8-yl]-N-(3-methoxy-propyl)-acetamide

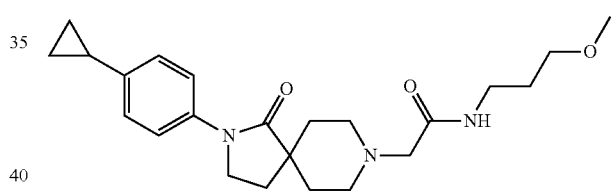

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from [2-(4-Cyclopropyl-phenyl)-1-oxo-2,8-diaza-spiro[4.5]dec-8-yl]-acetic acid and 3-methoxy-propylamine. MS m/e: 400.4 [M+H]⁺.

Example 18

N-Butyl-3-[2-(4-cyclopropyl-phenyl)-1-oxo-2,8-diaza-spiro[4.5]dec-8-yl]-propionamide

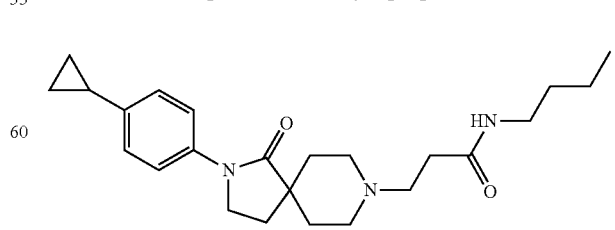

Step 1

3-[2-(4-Cyclopropyl-phenyl)-1-oxo-2,8-diaza-spiro[4.5]dec-8-yl]-propionic acid

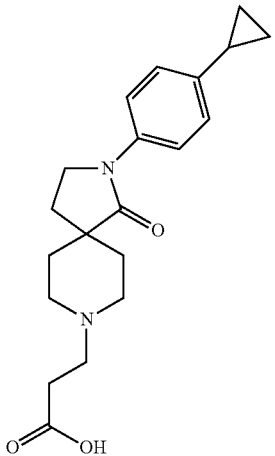 [SMILES: O=C(O)CCN1CCC2(CC1)CCN(c1ccc(C3CC3)cc1)C2=O]

In analogy to the procedure described for the synthesis of [2-(4-Cyclopropyl-phenyl)-1-oxo-2,8-diaza-spiro[4.5]dec-8-yl]-acetic acid (example 9, step 1) the title compound was prepared from 2-(4-Cyclopropyl-phenyl)-2,8-diaza-spiro[4.5]decan-1-one and 3-bromo-propionic acid. MS m/e: 343.3 [M+H]$^+$.

Step 2

N-Butyl-3-[2-(4-cyclopropyl-phenyl)-1-oxo-2,8-diaza-spiro[4.5]dec-8-yl]-propionamide In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 3-[2-(4-Cyclopropyl-phenyl)-1-oxo-2,8-diaza-spiro[4.5]dec-8-yl]-propionic acid and butylamine. MS m/e: 398.4 [M+H]$^+$.

Example 19

3-[2-(4-Cyclopropyl-phenyl)-1-oxo-2,8-diaza-spiro[4.5]dec-8-yl]-N-(4-trifluoromethyl-benzyl)-propionamide

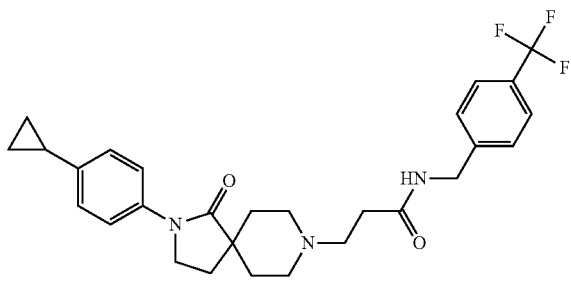 [SMILES: O=C(CCN1CCC2(CC1)CCN(c1ccc(C3CC3)cc1)C2=O)NCc1ccc(C(F)(F)F)cc1]

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 3-[2-(4-Cyclopropyl-phenyl)-1-oxo-2,8-diaza-spiro[4.5]dec-8-yl]-propionic acid and 4-trifluoromethyl-benzylamine. MS m/e: 500.4 [M+H]$^+$.

Example 20

3-[2-(4-Cyclopropyl-phenyl)-1-oxo-2,8-diaza-spiro[4.5]dec-8-yl]-N-(4-fluoro-phenyl)-propionamide

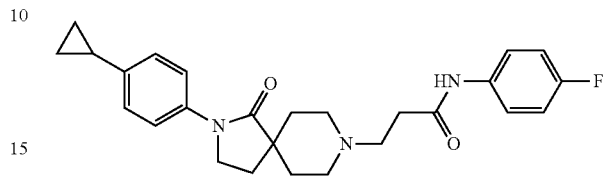

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 3-[2-(4-Cyclopropyl-phenyl)-1-oxo-2,8-diaza-spiro[4.5]dec-8-yl]-propionic acid and 4-fluoro-phenylamine. MS m/e: 436.4 [M+H]$^+$.

Example 21

N-Benzyl-3-[2-(4-cyclopropyl-phenyl)-1-oxo-2,8-diaza-spiro[4.5]dec-8-yl]-N-methyl-propionamide

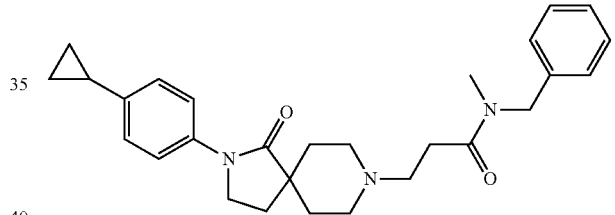

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 3-[2-(4-Cyclopropyl-phenyl)-1-oxo-2,8-diaza-spiro[4.5]dec-8-yl]-propionic acid and benzyl-methyl-amine. MS m/e: 446.4 [M+H]$^+$.

Example 22

N-Cyclohexyl-3-[2-(4-cyclopropyl-phenyl)-1-oxo-2,8-diaza-spiro[4.5]dec-8-yl]-N-methyl-propionamide

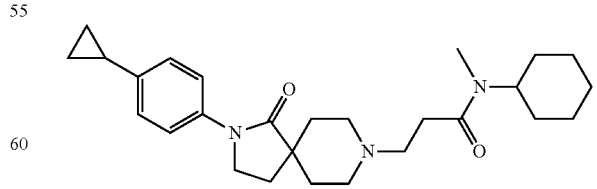

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 3-[2-(4-Cyclopropyl-phenyl)-1-oxo-2,8- diaza-spiro[4.5]dec-8-yl]-propionic acid and cyclohexyl-methyl-amine. MS m/e: 438.4 [M+H]⁺.

Example 23

2-(4-Cyclopropyl-phenyl)-8-(2-hydroxy-2-phenyl-ethyl)-2,8-diaza-spiro[4.5]decan-1-one

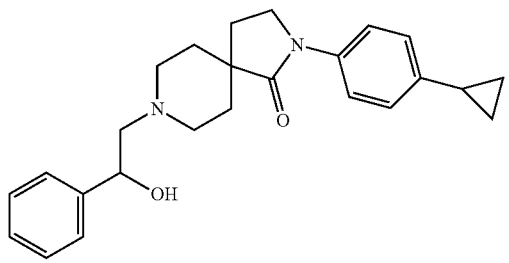 [SMILES: O=C1N(c2ccc(C3CC3)cc2)CCC12CCN(CC(O)c1ccccc1)CC2]

A mixture of 34.6 mg (0.128 mmol) 2-(4-Cyclopropyl-phenyl)-2,8-diaza-spiro[4.5]decan-1-one, 23 mg (0.192 mmol) 2-phenyl-oxirane and 38 mg (0.384 mmol) NEt₃ in 2 mL DCM were stirred at 50° C. for 2 h and concentrated. The residue was taken up in methanol and subjected to purification by preparative HPLC on reversed phase eluting with a gradient formed from acetonitrile, water and NEt₃. The product containing fractions were evaporated to yield 7.1 mg (14%) of the title compound. MS m/e: 391.4 [M+H]⁺.

Example 24

8-[2-(4-Chloro-phenyl)-2-hydroxy-ethyl]-2-(4-cyclopropyl-phenyl)-2,8-diaza-spiro[4.5]decan-1-one

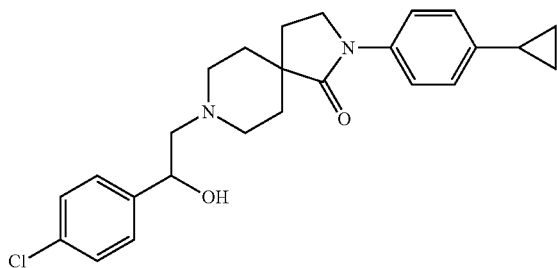 [SMILES: O=C1N(c2ccc(C3CC3)cc2)CCC12CCN(CC(O)c1ccc(Cl)cc1)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and 2-(4-chloro-phenyl)-oxirane. MS m/e: 425.4 [M+H]+.

Example 25

2-[2-(4-Cyclopropyl-phenyl)-1-oxo-2,8-diaza-spiro[4.5]dec-8-yl]-N-(4-fluoro-phenyl)-propionamide

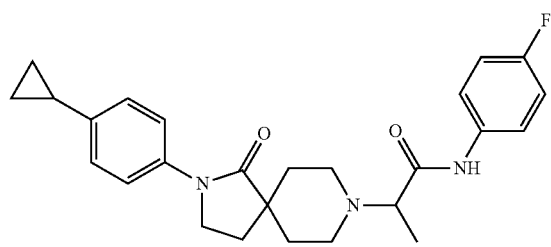 [SMILES: CC(C(=O)Nc1ccc(F)cc1)N1CCC2(CCN(c3ccc(C4CC4)cc3)C2=O)CC1]

Step 1

2-[2-(4-Cyclopropyl-phenyl)-1-oxo-2,8-diaza-spiro[4.5]dec-8-yl]-propionic acid

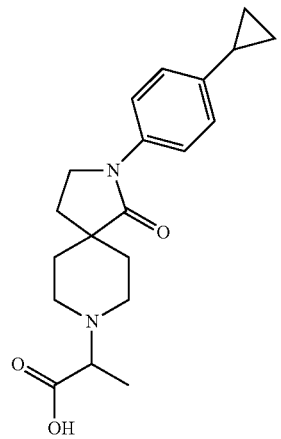 [SMILES: CC(C(=O)O)N1CCC2(CCN(c3ccc(C4CC4)cc3)C2=O)CC1]

A mixture of 200 mg (0.74 mmol) 2-(4-Cyclopropyl-phenyl)-2,8-diaza-spiro[4.5]decan-1-one, 168 mg (1.11 mmol) 2-bromo-propionic acid and 224 mg (2.21 mmol) NEt₃ in 5 mL DCE was heated to 80° C. for 2 h and concentrated. The residue was taken up in methanol and subjected to purification by preparative HPLC on reversed phase eluting with a gradient formed from acetonitrile, water and formic acid. The product containing fractions were evaporated to yield 49.4 mg (19%) of the title compound. MS m/e: 343.2 [M+H]⁺.

Step 2

2-[2-(4-Cyclopropyl-phenyl)-1-oxo-2,8-diaza-spiro[4.5]dec-8-yl]-N-(4-fluoro-phenyl)-propionamide In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 2-[2-(4-Cyclopropyl-phenyl)-1-oxo-2,8-diaza-spiro[4.5]dec-8-yl]-propionic acid and 4-fluoro-phenylamine. MS m/e: 436.3 [M+H]⁺.

Example 26

2-[2-(4-Cyclopropyl-phenyl)-1-oxo-2,8-diaza-spiro[4.5]dec-8-yl]-N-(4-fluoro-phenyl)-butyramide

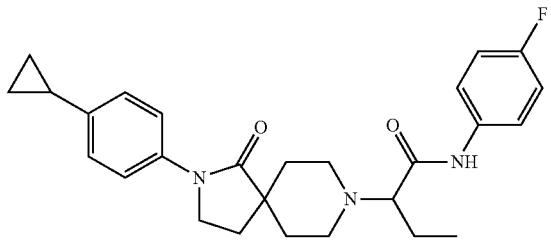 [SMILES: CCC(C(=O)Nc1ccc(F)cc1)N1CCC2(CCN(c3ccc(C4CC4)cc3)C2=O)CC1]

Step 1

2-[2-(4-Cyclopropyl-phenyl)-1-oxo-2,8-diaza-spiro[4.5]dec-8-yl]-butyric acid

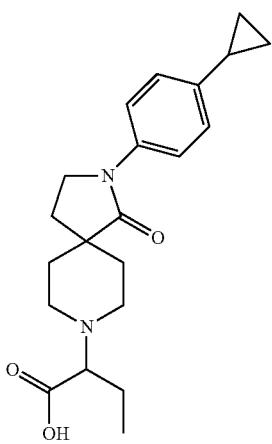 [SMILES: CCC(C(=O)O)N1CCC2(CCN(c3ccc(C4CC4)cc3)C2=O)CC1]

In analogy to the procedure described for the synthesis of 2-[2-(4-Cyclopropyl-phenyl)-1-oxo-2,8-diaza-spiro[4.5]dec-8-yl]-propionic acid (example 25, step 1) the title compound was prepared from 2-(4-Cyclopropyl-phenyl)-2,8-diaza-spiro[4.5]decan-1-one and 2-bromo-butyric acid. MS m/e: 357.3 [M+H]⁺.

Step 2

2-[2-(4-Cyclopropyl-phenyl)-1-oxo-2,8-diaza-spiro[4.5]dec-8-yl]-N-(4-fluoro-phenyl)-butyramide In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 2-[2-(4-Cyclopropyl-phenyl)-1-oxo-2,8-diaza-spiro[4.5]dec-8-yl]-butyric acid and 4-fluoro-phenylamine. MS m/e: 450.4 [M+H]⁺.

Example 27

N-Butyl-2-[2-(4-cyclopropyl-phenyl)-1-oxo-2,8-diaza-spiro[4.5]dec-8-yl]-propionamide

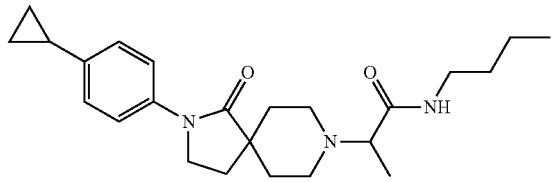 [SMILES: CCCCNC(=O)C(C)N1CCC2(CCN(c3ccc(C4CC4)cc3)C2=O)CC1]

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 2-[2-(4-Cyclopropyl-phenyl)-1-oxo-2,8-diaza-spiro[4.5]dec-8-yl]-propionic acid and butylamine. MS m/e: 398.4 [M+H]⁺.

Example 28

N-Butyl-2-[2-(4-cyclopropyl-phenyl)-1-oxo-2,8-diaza-spiro[4.5]dec-8-yl]-butyramide

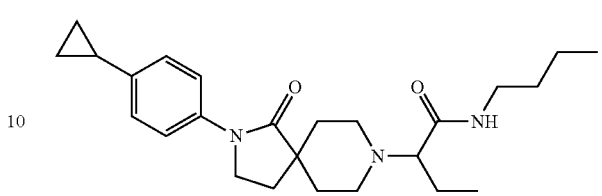

In analogy to the procedure described for the synthesis of 2-[2-(4-Cyclopropyl-phenyl)-1-oxo-2,8-diaza-spiro[4.5]dec-8-yl]-N-ethyl-acetamide (example 9) the title compound was prepared from 2-[2-(4-Cyclopropyl-phenyl)-1-oxo-2,8-diaza-spiro[4.5]dec-8-yl]-butyric acid and butylamine. MS m/e: 412.3 [M+H]⁺.

Example 29

N-Butyl-2-[2-(4-cyclopropyl-phenyl)-1-oxo-2,8-diaza-spiro[4.5]dec-8-yl]-2-phenyl-acetamide

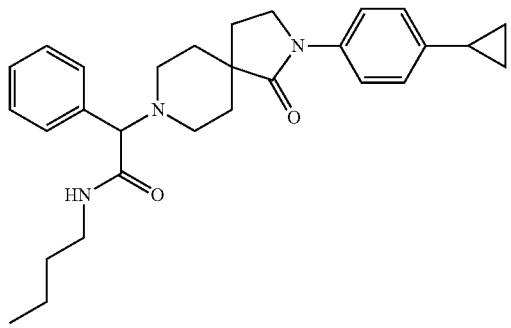 [SMILES: CCCCNC(=O)C(c1ccccc1)N1CCC2(CCN(c3ccc(C4CC4)cc3)C2=O)CC1]

Step 1

[2-(4-Cyclopropyl-phenyl)-1-oxo-2,8-diaza-spiro[4.5]dec-8-yl]-phenyl-acetic acid

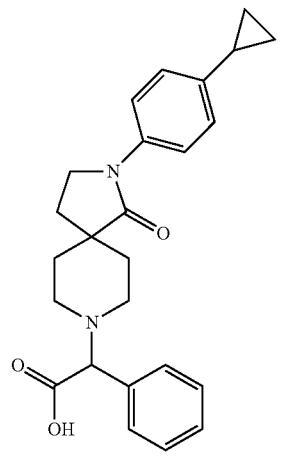 [SMILES: O=C(O)C(c1ccccc1)N1CCC2(CCN(c3ccc(C4CC4)cc3)C2=O)CC1]

In analogy to the procedure described for the synthesis of 2-[2-(4-Cyclopropyl-phenyl)-1-oxo-2,8-diaza-spiro[4.5]

dec-8-yl]-propionic acid (example 25, step 1) the title compound was prepared from 2-(4-Cyclopropyl-phenyl)-2,8-diaza-spiro[4.5]decan-1-one and bromo-phenyl-acetic acid. MS m/e: 460.4 [M+H]⁺.

Step 2

N-Butyl-2-[2-(4-cyclopropyl-phenyl)-1-oxo-2,8-diaza-spiro[4.5]dec-8-yl]-2-phenyl-acetamide In analogy to the procedure described for the synthesis of 2-[2-(4-Cyclopropyl-phenyl)-1-oxo-2,8-diaza-spiro[4.5] dec-8-yl]-N-ethyl-acetamide (example 9) the title compound was prepared from [2-(4-Cyclopropyl-phenyl)-1-oxo-2,8-diaza-spiro[4.5]dec-8-yl]-phenyl-acetic acid and butylamine. MS m/e: 460.4 [M+H]⁺.

Example 30

2-[2-(4-Cyclopropyl-phenyl)-1-oxo-2,8-diaza-spiro[4.5]dec-8-yl]-hexanoic acid butylamide

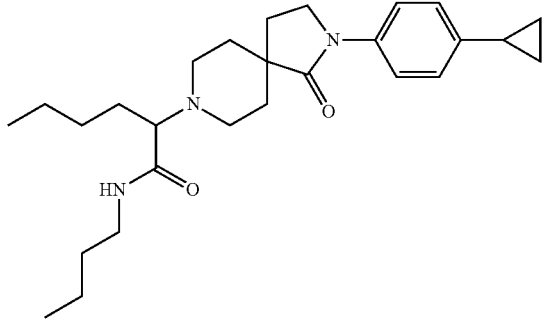 [SMILES: CCCCNC(=O)C(CCCC)N1CCC2(CCN(c3ccc(C4CC4)cc3)C2=O)CC1]

Step 1

2-[2-(4-Cyclopropyl-phenyl)-1-oxo-2,8-diaza-spiro[4.5]dec-8-yl]-hexanoic acid

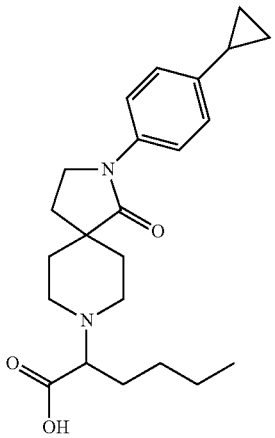 [SMILES: CCCCC(C(=O)O)N1CCC2(CCN(c3ccc(C4CC4)cc3)C2=O)CC1]

In analogy to the procedure described for the synthesis of 2-[2-(4-Cyclopropyl-phenyl)-1-oxo-2,8-diaza-spiro[4.5] dec-8-yl]-propionic acid (example 25, step 1) the title compound was prepared from 2-(4-Cyclopropyl-phenyl)-2,8-diaza-spiro[4.5]decan-1-one and 2-bromo-hexanoic acid. MS m/e: 385.3 [M+H]⁺.

Step 2

2-[2-(4-Cyclopropyl-phenyl)-1-oxo-2,8-diaza-spiro[4.5]dec-8-yl]-hexanoic acid butylamide In analogy to the procedure described for the synthesis of 2-[2-(4-Cyclopropyl-phenyl)-1-oxo-2,8-diaza-spiro[4.5] dec-8-yl]-N-ethyl-acetamide (example 9) the title compound was prepared from 2-[2-(4-Cyclopropyl-phenyl)-1-oxo-2,8-diaza-spiro[4.5]dec-8-yl]-hexanoic acid and butylamine. MS m/e: 440.4 [M+H]⁺.

Example 31

N-Butyl-2-[2-(4-cyclopropyl-phenyl)-1-oxo-2,8-diaza-spiro[4.5]dec-8-yl]-3-methyl-butyramide

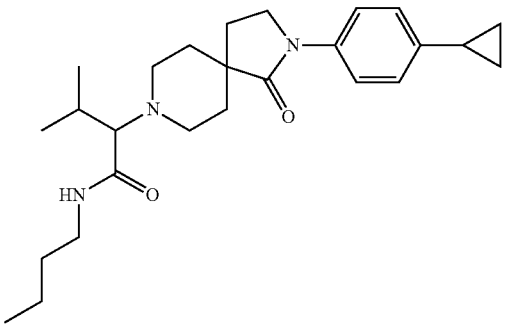 [SMILES: CCCCNC(=O)C(C(C)C)N1CCC2(CCN(c3ccc(C4CC4)cc3)C2=O)CC1]

Step 1

2-[2-(4-Cyclopropyl-phenyl)-1-oxo-2,8-diaza-spiro[4.5]dec-8-yl]-3-methyl-butyric acid In analogy to the procedure described for the synthesis of 2-[2-(4-Cyclopropyl-phenyl)-1-oxo-2,8-diaza-spiro[4.5] dec-8-yl]-propionic acid (example 25, step 1) the title compound was prepared from 2-(4-Cyclopropyl-phenyl)-2,8-diaza-spiro[4.5]decan-1-one and 2-bromo-3-methyl-butyric acid. MS m/e: 371.3 [M+H]⁺.

Step 2

N-Butyl-2-[2-(4-cyclopropyl-phenyl)-1-oxo-2,8-diaza-spiro[4.5]dec-8-yl]-3-methyl-butyramide In analogy to the procedure described for the synthesis of 2-[2-(4-Cyclopropyl-phenyl)-1-oxo-2,8-diaza-spiro[4.5]

dec-8-yl]-N-ethyl-acetamide (example 9) the title compound was prepared from 2-[2-(4-Cyclopropyl-phenyl)-1-oxo-2,8-diaza-spiro[4.5]dec-8-yl]-3-methyl-butyric acid and butylamine. MS m/e: 426.4 [M+H]⁺.

Example 32

2-(4-Cyclopropyl-phenyl)-8-((S)-2-hydroxy-2-phenyl-ethyl)-2,8-diaza-spiro[4.5]decan-1-one

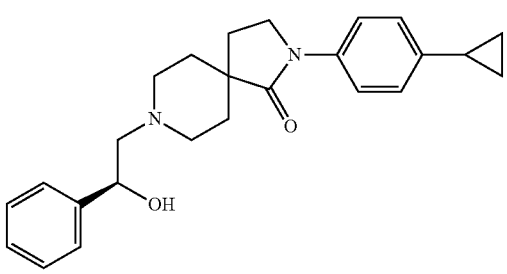 [SMILES: O=C1N(c2ccc(C3CC3)cc2)CCC12CCN(C[C@@H](O)c1ccccc1)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and (S)-2-phenyl-oxirane. MS m/e: 391.3 [M+H]+.

Example 33

2-(4-Cyclopropyl-phenyl)-8-((R)-2-hydroxy-2-phenyl-ethyl)-2,8-diaza-spiro[4.5]decan-1-one

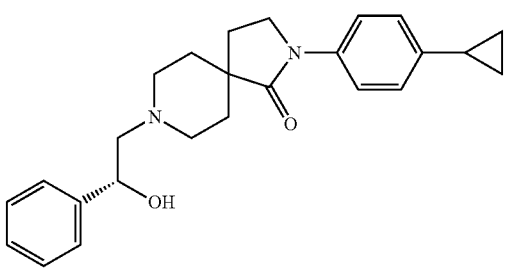 [SMILES: O=C1N(c2ccc(C3CC3)cc2)CCC12CCN(C[C@H](O)c1ccccc1)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and (R)-2-phenyl-oxirane. MS m/e: 391.3 [M+H]⁺.

Example 34

2-(4-Cyclopropyl-phenyl)-8-(2-hydroxy-2-phenyl-propyl)-2,8-diaza-spiro[4.5]decan-1-one

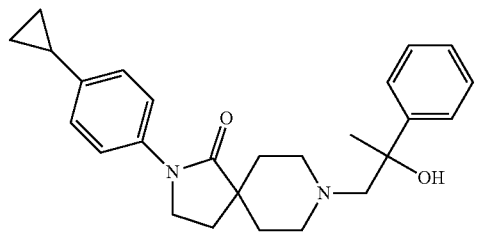 [SMILES: CC(O)(CN1CCC2(CC1)CCN(c1ccc(C3CC3)cc1)C2=O)c1ccccc1]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and 2-methyl-2-phenyl-oxirane. MS m/e: 405.3 [M+H]⁺.

Example 35

2-(4-Cyclopropyl-phenyl)-8-[(R)-2-(4-fluoro-phenyl)-2-hydroxy-ethyl]-2,8-diaza-spiro[4.5]decan-1-one

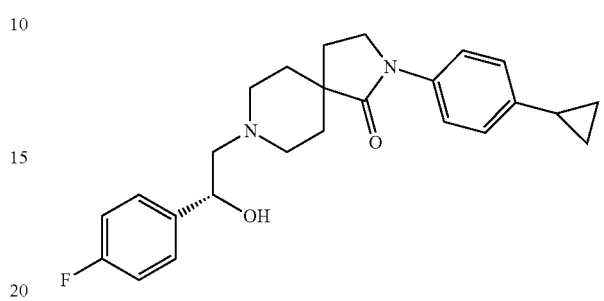

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and (R)-2-(4-fluoro-phenyl)-oxirane. MS m/e: 409.3 [M+H]⁺.

Example 36

8-[(R)-2-(3-Chloro-phenyl)-2-hydroxy-ethyl]-2-(4-cyclopropyl-phenyl)-2,8-diaza-spiro[4.5]decan-1-one

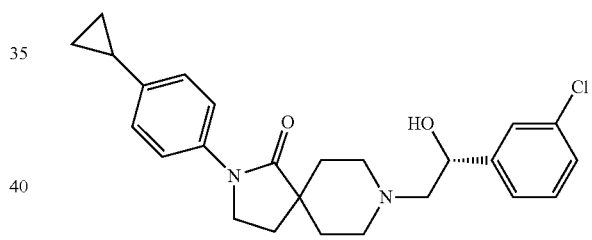

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and (R)-2-(3-chloro-phenyl)-oxirane. MS m/e: 425.3 [M+H]⁺.

Example 37

2-(4-Cyclopropyl-phenyl)-8-[2-(3,4-dichloro-phenyl)-2-hydroxy-ethyl]-2,8-diaza-spiro[4.5]decan-1-one

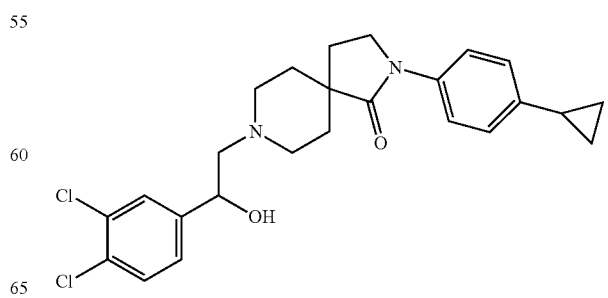

In analogy to the procedure described for the synthesis of 2-(4-Cyclopropyl-phenyl)-8-(2-hydroxy-2-phenyl-ethyl)-2, 8-diaza-spiro[4.5]decan-1-one (example 23) the title compound was prepared from 2-(4-Cyclopropyl-phenyl)-2,8-diaza-spiro[4.5]decan-1-one and (R)-2-(3,4-dichloro-phenyl)-oxirane. MS m/e: 459.3 [M+H]+.

Example 38

2-(4-Cyclopropyl-phenyl)-8-[2-(2,4-dichloro-phenyl)-2-hydroxy-ethyl]-2,8-diaza-spiro[4.5]decan-1-one

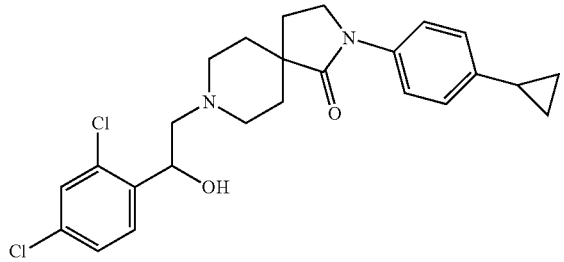 [SMILES: O=C1N(c2ccc(C3CC3)cc2)CCC12CCN(CC(O)c1ccc(Cl)cc1Cl)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and 2-(2,4-dichloro-phenyl)-oxirane. MS m/e: 459.3 [M+H]+.

Example 39

8-[2-(2-Chloro-6-fluoro-phenyl)-2-hydroxy-ethyl]-2-(4-cyclopropyl-phenyl)-2,8-diaza-spiro[4.5]decan-1-one

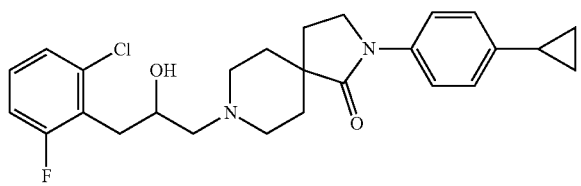 [SMILES: O=C1N(c2ccc(C3CC3)cc2)CCC12CCN(CC(O)Cc1c(F)cccc1Cl)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and 2-(2-Chloro-6-fluoro-benzyl)-oxirane. MS m/e: 443.3 [M+H]+.

Example 40

3-[2-(4-Cyclopropyl-phenyl)-1-oxo-2,8-diaza-spiro[4.5]dec-8-yl]-2-hydroxy-3-(4-methoxy-phenyl)-propionamide

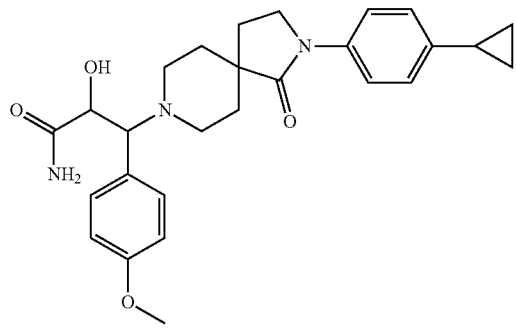 [SMILES: COc1ccc(C(C(O)C(N)=O)N2CCC3(CCN(c4ccc(C5CC5)cc4)C3=O)CC2)cc1]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-(4-Cyclopropyl-phenyl)-2,8-diaza-spiro[4.5]decan-1-one and 3-(4-Methoxy-phenyl)-oxirane-2-carboxylic acid amide. MS m/e: 464.4 [M+H]+.

Example 41

(S)-2-[2-(4-Cyclopropyl-phenyl)-1-oxo-2,8-diaza-spiro[4.5]dec-8-yl]-hexanoic acid butylamide

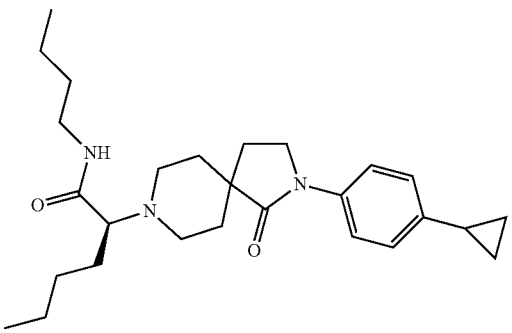 [SMILES: CCCCNC(=O)[C@H](CCCC)N1CCC2(CCN(c3ccc(C4CC4)cc3)C2=O)CC1]

The title compound was accessed from 2-[2-(4-Cyclopropyl-phenyl)-1-oxo-2,8-diaza-spiro[4.5]dec-8-yl]-hexanoic acid butylamide (example 30) through separation by chiral HPLC. MS m/e: 464.4 [M+H]+.

Example 42

(R)-2-[2-(4-Cyclopropyl-phenyl)-1-oxo-2,8-diaza-spiro[4.5]dec-8-yl]-hexanoic acid butylamide

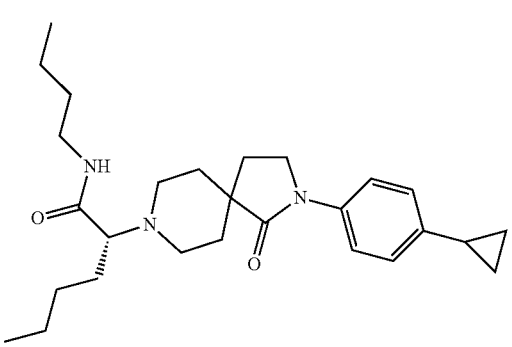 [SMILES: CCCCNC(=O)[C@@H](CCCC)N1CCC2(CCN(c3ccc(C4CC4)cc3)C2=O)CC1]

The title compound was accessed from 2-[2-(4-Cyclopropyl-phenyl)-1-oxo-2,8-diaza-spiro[4.5]dec-8-yl]-hexanoic acid butylamide (example 30) through separation by chiral HPLC. MS m/e: 464.4 [M+H]+.

Example 43

8-[2-(2,4-Dichloro-phenyl)-2-oxo-ethyl]-2-(4-ethyl-phenyl)-2,8-diaza-spiro[4.5]decan-1-one

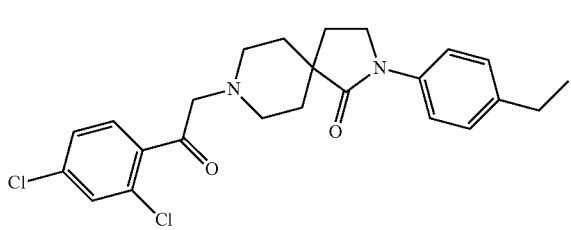 [SMILES: CCc1ccc(N2CCC3(CCN(CC(=O)c4ccc(Cl)cc4Cl)CC3)C2=O)cc1]

Step 1

2-(4-Ethyl-phenyl)-2,8-diaza-spiro[4.5]decan-1-one

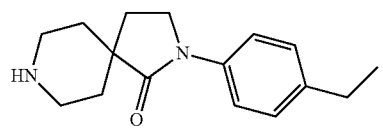 [SMILES: CCc1ccc(N2CCC3(CCNCC3)C2=O)cc1]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 4-Ethyl-phenylamine. MS m/e: 259.2 [M+H]+.

Step 2

A mixture of 320 mg (1.24 mmol) 2-(4-ethylphenyl)-2,8-diazaspiro[4.5]decan-1-one, 431 mg (1.61 mmol) 2-bromo-1-(2,4-dichlorophenyl)ethanone and 376 mg (3.72 mmol) triethylamine in 50 mL DCM was stirred at 22° C. for 16 h. The crude reaction mixture was concentrated in vacuo. The crude material was purified by flash chromatography on silica eluting with a gradient formed from ethyl acetate and heptane to yield after evaporation of the product containing fractions 435 mg (79%) of the title compound as orange solid. MS m/e: 445.2 [M+H]+.

Example 44

8-[2-(2,4-Dichloro-phenyl)-2-hydroxy-ethyl]-2-[4-(2,2,2-trifluoro-ethoxy)-phenyl]-2,8-diaza-spiro[4.5]decan-1-one

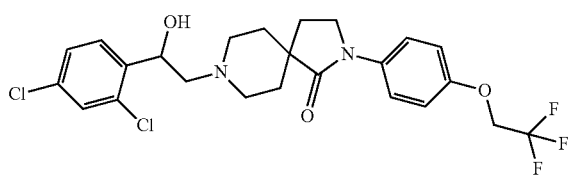 [SMILES: O=C1N(c2ccc(OCC(F)(F)F)cc2)CCC12CCN(CC(O)c1ccc(Cl)cc1Cl)CC2]

Step 1

2-[4-(2,2,2-Trifluoro-ethoxy)-phenyl]-2,8-diaza-spiro[4.5]decan-1-one

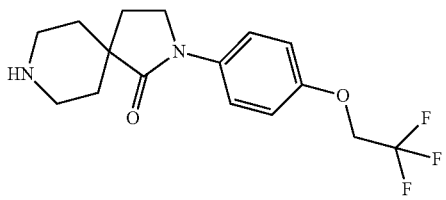 [SMILES: O=C1N(c2ccc(OCC(F)(F)F)cc2)CCC12CCNCC2]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 4-(2,2,2-Trifluoro-ethoxy)-phenylamine. MS m/e: 329.2 [M+H]+.

Step 2

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-(2,2,2-Trifluoro-ethoxy)-phenyl]-2,8-diaza-spiro[4.5]decan-1-one and 2-(2,4-Dichloro-phenyl)-oxirane. MS m/e: 517.3 [M+H]+.

Example 45

8-[2-(2,4-Dichloro-phenyl)-2-hydroxy-ethyl]-2-[6-((R)-2,2,2-trifluoro-1-methyl-ethoxy)-pyridin-3-yl]-2,8-diaza-spiro[4.5]decan-1-one

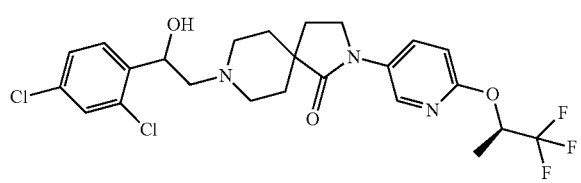 [SMILES: C[C@@H](Oc1ccc(N2CCC3(CCN(CC(O)c4ccc(Cl)cc4Cl)CC3)C2=O)cn1)C(F)(F)F]

Step 1

2-[6-((R)-2,2,2-Trifluoro-1-methyl-ethoxy)-pyridin-3-yl]-2,8-diaza-spiro[4.5]decan-1-one

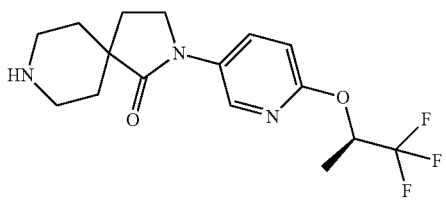 [SMILES: C[C@@H](Oc1ccc(N2CCC3(CCNCC3)C2=O)cn1)C(F)(F)F]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 6-((R)-2,2,2-Trifluoro-1-methyl-ethoxy)-pyridin-3-ylamine. MS m/e: 344.2 [M+H]+.

Step 2

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[6-((R)-2,2,2-Trifluoro-1-methyl-ethoxy)-pyridin-3-yl]-2,8-diaza-spiro[4.5]decan-1-one and 2-(2,4-Dichloro-phenyl)-oxirane. MS m/e: 532.3 [M+H]+.

Example 46

8-[2-(2,4-Dichloro-phenyl)-2-hydroxy-ethyl]-2-[4-(2,2,2-trifluoro-ethyl)-phenyl]-2,8-diaza-spiro[4.5]decan-1-one

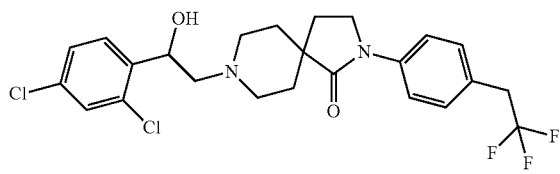 [SMILES: O=C1N(c2ccc(CC(F)(F)F)cc2)CCC12CCN(CC(O)c1ccc(Cl)cc1Cl)CC2]

Step 1

2-[4-(2,2,2-Trifluoro-ethyl)-phenyl]-2,8-diaza-spiro[4.5]decan-1-one

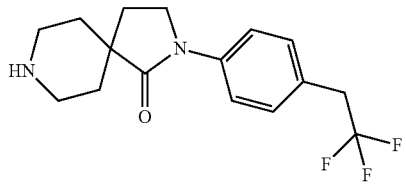 [SMILES: O=C1N(c2ccc(CC(F)(F)F)cc2)CCC12CCNCC2]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 4-(2,2,2-Trifluoro-ethyl)-phenylamine. MS m/e: 313.2 [M+H]+.

Step 2

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-(2,2,2-Trifluoro-ethyl)-phenyl]-2,8-diaza-spiro[4.5]decan-1-one and 2-(2,4-Dichlorophenyl)-oxirane. MS m/e: 501.3 [M+H]+.

Example 47

8-[2-(2-Chloro-6-fluoro-phenyl)-2-hydroxy-ethyl]-2-[4-(2,2,2-trifluoro-ethoxy)-phenyl]-2,8-diaza-spiro[4.5]decan-1-one

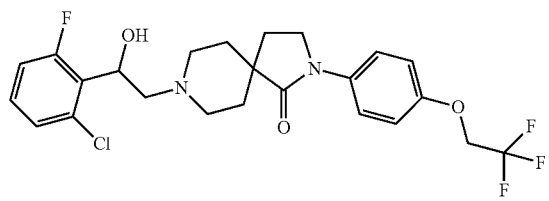 [SMILES: O=C1N(c2ccc(OCC(F)(F)F)cc2)CCC12CCN(CC(O)c1c(F)cccc1Cl)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-(2,2,2-Trifluoro-ethoxy)-phenyl]-2,8-diaza-spiro[4.5]decan-1-one and 2-(2-Chloro-6-fluoro-phenyl)-oxirane. MS m/e: 501.3 [M+H]+.

Example 48

8-[2-(2-Chloro-6-fluoro-phenyl)-2-hydroxy-ethyl]-2-[4-((R)-2,2,2-trifluoro-1-methyl-ethoxy)-phenyl]-2,8-diaza-spiro[4.5]decan-1-one

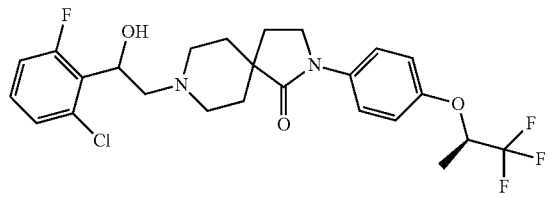 [SMILES: C[C@@H](Oc1ccc(N2CCC3(CCN(CC(O)c4c(F)cccc4Cl)CC3)C2=O)cc1)C(F)(F)F]

Step 1

2-[4-((R)-2,2,2-Trifluoro-1-methyl-ethoxy)-phenyl]-2,8-diaza-spiro[4.5]decan-1-one

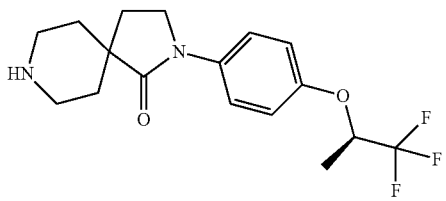 [SMILES: C[C@@H](Oc1ccc(N2CCC3(CCNCC3)C2=O)cc1)C(F)(F)F]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 4-((R)-2,2,2-Trifluoro-1-methyl-ethoxy)-phenylamine. MS m/e: 343.2 [M+H]+.

Step 2

In analogy to the procedure described for the synthesis of 2-(4-Cyclopropyl-phenyl)-8-(2-hydroxy-2-phenyl-ethyl)-2, 8-diaza-spiro[4.5]decan-1-one (example 23) the title compound was prepared from 2-[4-((R)-2,2,2-Trifluoro-1-methyl-ethoxy)-phenyl]-2,8-diaza-spiro[4.5]decan-1-one and 2-(2-Chloro-6-fluoro-phenyl)-oxirane. MS m/e: 515.3 [M+H]+.

Example 49

8-[2-(2-Chloro-6-fluoro-phenyl)-2-hydroxy-ethyl]-2-[6-((R)-2,2,2-trifluoro-1-methyl-ethoxy)-pyridin-3-yl]-2,8-diaza-spiro[4.5]decan-1-one

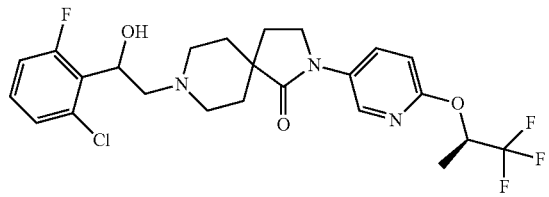 [SMILES: C[C@@H](Oc1ccc(N2CCC3(CCN(CC(O)c4c(F)cccc4Cl)CC3)C2=O)cn1)C(F)(F)F]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[6-((R)-2,2,2-Trifluoro-1-methyl-ethoxy)-pyridin-3-yl]-2,8-diaza-spiro[4.5]decan-1-one and 2-(2-Chloro-6-fluoro-phenyl)-oxirane. MS m/e: 516.3 [M+H]+.

Example 50

8-[2-(2-Chloro-6-fluoro-phenyl)-2-hydroxy-ethyl]-2-[4-(2,2,2-trifluoro-ethyl)-phenyl]-2,8-diaza-spiro[4.5]decan-1-one

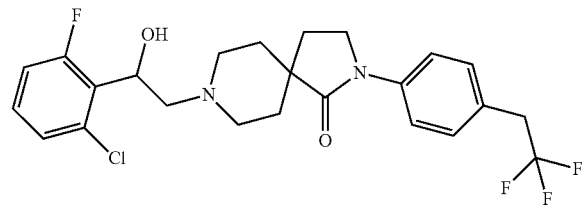 [SMILES: O=C1N(c2ccc(CC(F)(F)F)cc2)CCC12CCN(CC(O)c1c(F)cccc1Cl)CC2]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-(2,2,2-Trifluoro-ethyl)-phenyl]-2,8-diaza-spiro[4.5]decan-1-one and 2-(2-Chloro-6-fluoro-phenyl)-oxirane. MS m/e: 485.3 [M+H]+.

Example 51

8-[2-(2,4-Dichloro-phenyl)-2-hydroxy-ethyl]-2-[4-((R)-2,2,2-trifluoro-1-methyl-ethoxy)-phenyl]-2,8-diaza-spiro[4.5]decan-1-one

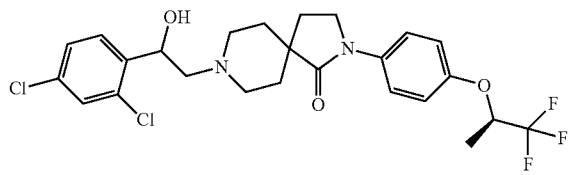 [SMILES: C[C@@H](Oc1ccc(N2CCC3(CCN(CC(O)c4ccc(Cl)cc4Cl)CC3)C2=O)cc1)C(F)(F)F]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-((R)-2,2,2-Trifluoro-1-methyl-ethoxy)-phenyl]-2,8-diaza-spiro[4.5]decan-1-one and 2-(2,4-Dichloro-phenyl)-oxirane. MS m/e: 531.3 [M+H]+.

Example 52

8-[2-(2,4-Dichloro-phenyl)-2-hydroxy-ethyl]-2-[4-((S)-2,2,2-trifluoro-1-methyl-ethoxy)-phenyl]-2,8-diaza-spiro[4.5]decan-1-one

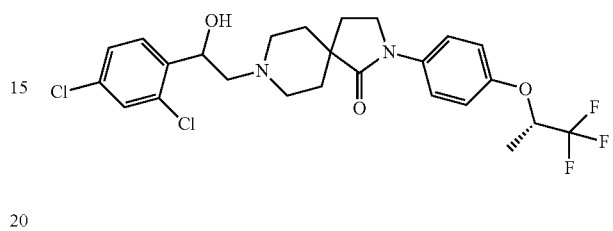

Step 1

2-[4-((S)-2,2,2-Trifluoro-1-methyl-ethoxy)-phenyl]-2,8-diaza-spiro[4.5]decan-1-one

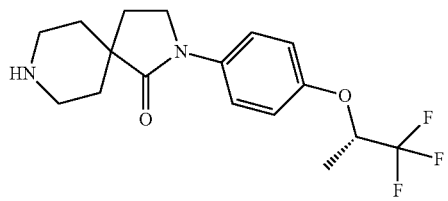 [SMILES: C[C@H](Oc1ccc(N2CCC3(CCNCC3)C2=O)cc1)C(F)(F)F]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 4-((S)-2,2,2-Trifluoro-1-methyl-ethoxy)-phenylamine. MS m/e: 343.2 [M+H]+.

Step 2

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-((S)-2,2,2-Trifluoro-1-methyl-ethoxy)-phenyl]-2,8-diaza-spiro[4.5]decan-1-one and 2-(2,4-Dichloro-phenyl)-oxirane. MS m/e: 531.3 [M+H]+.

Example 53

8-[2-(2,4-Dichloro-phenyl)-2-hydroxy-ethyl]-2-[6-((S)-2,2,2-trifluoro-1-methyl-ethoxy)-pyridin-3-yl]-2,8-diaza-spiro[4.5]decan-1-one

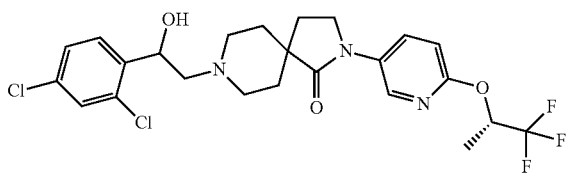 [SMILES: C[C@H](Oc1ccc(N2CCC3(CCN(CC(O)c4ccc(Cl)cc4Cl)CC3)C2=O)cn1)C(F)(F)F]

Step 1

2-[6-((S)-2,2,2-Trifluoro-1-methyl-ethoxy)-pyridin-3-yl]-2,8-diaza-spiro[4.5]decan-1-one

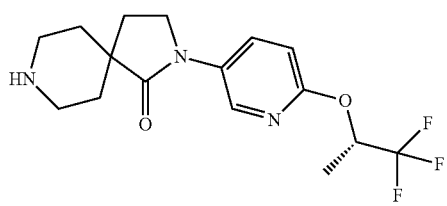 [SMILES: C[C@H](Oc1ccc(N2CCC3(CCNCC3)C2=O)cn1)C(F)(F)F]

In analogy to the procedure described for the synthesis of 2-(4-Cyclopropyl-phenyl)-8-(3-phenyl-propyl)-2,8-diaza-spiro[4.5]decan-1-one (example 1, step 2) the title compound was prepared from 4-(2-Methoxy-ethyl)-piperidine-1,4-dicarboxylic acid 1-tert-butyl ester 4-ethyl ester and 6-((S)-2,2,2-Trifluoro-1-methyl-ethoxy)-pyridin-3-ylamine. MS m/e: 344.2 [M+H]+.

Step 2

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[6-((S)-2,2,2-Trifluoro-1-methyl-ethoxy)-pyridin-3-yl]-2,8-diaza-spiro[4.5]decan-1-one and 2-(2,4-Dichloro-phenyl)-oxirane. MS m/e: 532.3 [M+H]+.

Example 54

8-[2-(2-Chloro-6-fluoro-phenyl)-2-hydroxy-ethyl]-2-[4-((S)-2,2,2-trifluoro-1-methyl-ethoxy)-phenyl]-2,8-diaza-spiro[4.5]decan-1-one

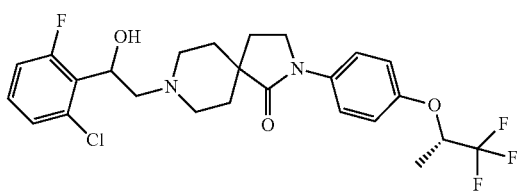 [SMILES: C[C@H](Oc1ccc(N2CCC3(CCN(CC(O)c4c(F)cccc4Cl)CC3)C2=O)cc1)C(F)(F)F]

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[4-((S)-2,2,2-Trifluoro-1-methyl-ethoxy)-phenyl]-2,8-diaza-spiro[4.5]decan-1-one and 2-(2-Chloro-6-fluoro-phenyl)-oxirane. MS m/e: 515.3 [M+H]+.

Example 55

8-[2-(2-Chloro-6-fluoro-phenyl)-2-hydroxy-ethyl]-2-[6-((S)-2,2,2-trifluoro-1-methyl-ethoxy)-pyridin-3-yl]-2,8-diaza-spiro[4.5]decan-1-one

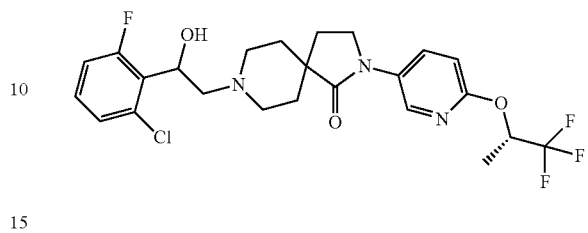

In analogy to the procedure described for the synthesis of 2-(4-Cyclopropyl-phenyl)-8-(2-hydroxy-2-phenyl-ethyl)-2,8-diaza-spiro[4.5]decan-1-one (example 23) the title compound was prepared from 2-[6-((S)-2,2,2-Trifluoro-1-methyl-ethoxy)-pyridin-3-yl]-2,8-diaza-spiro[4.5]decan-1-one and 2-(2-Chloro-6-fluoro-phenyl)-oxirane. MS m/e: 516.3 [M+H]+.

Example 56

A compound according to formula (I) as described above can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 57

A compound according to formula (I) as described above can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example 58

Production of Human Full Length Hormone Sensitive Lipase-His[6]

1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His$^6$, 48 hr., containing 25 μM E-64. Cell count: $1.78 \times 10^{10}$ cells/ml, 90% viable. Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with 3.75×107 cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 μm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 μm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 μm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

The following table lists the results of the foregoing HSL enzyme inhibition assay (uM means microMolar).

| Examples | HSL hum IC$_{50}$ (uM) |
|---|---|
| 1 | 0.24 |
| 2 | 0.07 |
| 3 | 0.36 |
| 4 | 0.03 |
| 5 | 0.17 |
| 6 | 0.98 |
| 7 | 0.03 |
| 8 | 0.04 |
| 9 | 0.61 |
| 10 | 0.38 |
| 11 | 0.09 |
| 12 | 0.03 |
| 13 | 0.08 |
| 14 | 0.22 |
| 15 | 0.08 |
| 16 | 0.06 |
| 17 | 0.71 |
| 18 | 0.46 |
| 19 | 0.03 |
| 20 | 0.06 |
| 21 | 0.09 |
| 22 | 0.32 |
| 23 | 0.07 |
| 24 | 0.08 |
| 25 | 0.04 |
| 26 | 0.05 |
| 27 | 0.03 |
| 28 | 0.03 |
| 29 | 0.04 |
| 30 | 0.02 |
| 31 | 0.02 |
| 32 | 0.09 |
| 33 | 0.04 |
| 34 | 0.1 |
| 35 | 0.02 |
| 36 | 0.03 |
| 37 | 0.03 |
| 38 | 0.03 |
| 39 | 0.037 |
| 40 | 0.165 |
| 41 | 0.047 |
| 42 | 0.011 |
| 43 | 0.036 |
| 44 | 0.026 |
| 45 | 0.022 |
| 46 | 0.019 |
| 47 | 0.035 |
| 48 | 0.023 |
| 49 | 0.042 |
| 50 | 0.018 |
| 51 | 0.022 |
| 52 | 0.02 |
| 53 | 0.043 |
| 54 | 0.029 |
| 55 | 0.038 |

Example 59

The following describes a cellular assay used to measure the effect of the compounds to inhibit lipolysis in intact cells (adipocytes).

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

The invention claimed is:

1. A compound according to formula (I)

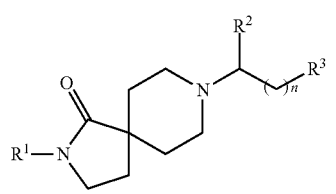

(I)

wherein
$R^1$ is substituted phenyl, wherein substituted phenyl is substituted with one to three substituents independently selected from the group consisting of: alkyl, cycloalkyl, haloalkyl, hydroxy, alkoxy, hydroxyalkoxy, alkoxyalkoxy, and haloalkoxy and, wherein substituted phenyl is optionally further substituted with one to two substituents independently selected from halogen;
$R^2$ is selected from the group consisting of: hydrogen, alkyl, cycloalkyl, phenyl, phenylalkyl, substituted phenyl or substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
$R^3$ is selected from the group consisting of: —$R^4$, —C(OH)$R^5R^6$ and —C(O)N$R^7R^8$;
$R^4$ is selected from the group consisting of: phenyl, phenylcarbonyl, phenylalkyl, substituted phenyl, substituted phenylcarbonyl and substituted phenylalkyl, wherein substituted phenyl, substituted phenylcarbonyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
one of $R^5$ and $R^6$ is selected from the group consisting of: hydrogen, alkyl and cycloalkyl and the other one is selected from the group consisting of: aminocarbonyl, phenyl, phenylalkyl, substituted phenyl or substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
one of $R^7$ and $R^8$ is selected from the group consisting of: hydrogen, alkyl, cycloalkyl, hydroxyalkyl and alkoxyalkyl and the other is selected from the group consisting of: alkyl, cycloalkyl, hydroxyalkyl, alkoxyalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
or $R^7$ and $R^8$ together with the nitrogen atom to which they are attached form pyrrolidinyl, piperidinyl, azepanyl, piperidazinyl, morpholinyl or thiomorpholinyl; and
n is zero or 1;
or a pharmaceutically acceptable salt thereof.

2. A compound according to claim 1, wherein
$R^1$ is substituted phenyl, wherein substituted phenyl is substituted with one to three substituents independently selected from the group consisting of: alkyl, cycloalkyl, haloalkyl, hydroxy, alkoxy, hydroxyalkoxy, alkoxyalkoxy, and haloalkoxy and wherein substituted phenyl is optionally further substituted with one to two substituents independently selected from halogen;
$R^2$ is selected from the group consisting of: hydrogen, alkyl, cycloalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
$R^3$ is selected from the group consisting of: —$R^4$, —C(OH)$R^5R^6$ and —C(O)N$R^7R^8$;
$R^4$ is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
one of $R^5$ and $R^6$ is selected from the group consisting of: hydrogen, alkyl and cycloalkyl and the one is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
one of $R^7$ and $R^8$ is selected from the group consisting of: hydrogen, alkyl, cycloalkyl, hydroxyalkyl and alkoxyalkyl and the other is selected from the group consisting of: alkyl, cycloalkyl, hydroxyalkyl, alkoxyalkyl, phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy;
or $R^7$ and $R^8$ together with the nitrogen atom to which they are attached form pyrrolidinyl, piperidinyl, azepanyl, piperidazinyl, morpholinyl or thiomorpholinyl; and
n is zero or 1;
or a pharmaceutically acceptable salt thereof.

3. A compound according to claim 1, wherein $R^1$ is substituted phenyl, wherein substituted phenyl is substituted with one to three substituents independently selected from cycloalkyl and haloalkoxy, and, wherein substituted phenyl is optionally further substituted with one to two substituents independently selected from halogen.

4. A compound according to claim 1, wherein $R^1$ is substituted phenyl, wherein substituted phenyl is substituted with one to three substituents independently selected from cycloalkyl.

5. A compound according to claim 1, wherein $R^3$ is —C(OH)$R^5R^6$.

6. A compound according to claim 1, wherein one of $R^5$ and $R^6$ is hydrogen and the other is selected from the group consisting of: phenyl, phenylalkyl, substituted phenyl and substituted phenylalkyl, wherein substituted phenyl and substituted phenylalkyl are substituted with one to three substituents independently selected from the group consisting of: alkyl, cycloalkyl, halogen, haloalkyl, hydroxy, alkoxy, hydroxyalkoxy, alkoxyalkoxy and haloalkoxy.

7. A compound according to claim 1, wherein one of $R^5$ and $R^6$ is hydrogen and the other is phenyl or substituted phenyl, wherein substituted phenyl is substituted with one to three substituents independently selected from halogen.

8. A compound according to claim 1, wherein $R^3$ is —C(O)N$R^7R^8$.

9. A compound according to claim 1, wherein one of $R^7$ and $R^8$ is hydrogen or alkyl and the other is selected from the group consisting of: alkyl, cycloalkyl, alkoxyalkyl, phenylalkyl, substituted phenyl and substituted phenylalkyl, wherein substituted phenyl and substituted phenylalkyl are substituted with one to three substituents independently selected from halogen and haloalkyl.

10. A compound according to claim 1, wherein one of $R^7$ and $R^8$ is hydrogen and the other is selected from the group consisting of: alkyl, substituted phenyl and substituted phenylalkyl, wherein substituted phenyl and substituted phenylalkyl are substituted with one to three substituents independently selected from halogen and haloalkyl.

11. A compound according to claim 1, wherein $R^4$ is selected from the group consisting of: phenyl, phenylalkyl and substituted phenyl, wherein substituted phenyl is substituted with one to three substituents independently selected from haloalkyl.

12. A compound according to claim 1, wherein $R^2$ is selected from the group consisting of: hydrogen, alkyl and phenyl.

13. A compound according to claim 1 selected from the group consisting of:
  2-(4-Cyclopropyl-phenyl)-8-(3-phenyl-propyl)-2,8-diaza-spiro[4.5]decan-1-one;
  2-(4-Cyclopropyl-phenyl)-8-phenethyl-2,8-diaza-spiro[4.5]decan-1-one;
  2-(4-Cyclopropyl-phenyl)-8-(4-trifluoromethyl-benzyl)-2,8-diaza-spiro[4.5]decan-1-one;
  2-(4-Cyclopropyl-phenyl)-8-(1-phenyl-ethyl)-2,8-diaza-spiro[4.5]decan-1-one;
  2-(4-Cyclopropyl-phenyl)-8-[1-(3-trifluoromethyl-phenyl)-ethyl]-2,8-diaza-spiro[4.5]decan-1-one;
  2-(2-Chloro-4-cyclopropyl-phenyl)-8-(1-phenyl-ethyl)-2,8-diaza-spiro[4.5]decan-1-one;
  2-(4-Cyclopropyl-phenyl)-8-(1-phenyl-propyl)-2,8-diaza-spiro[4.5]decan-1-one; and
  8-Benzyl-2-(4-trifluoromethoxy-phenyl)-2,8-diaza-spiro[4.5]decan-1-one.

14. A compound according to claim 1 selected from the group consisting of:
  2-(4-Cyclopropyl-phenyl)-8-(1-phenyl-propyl)-2,8-diaza-spiro[4.5]decan-1-one;
  N-Butyl-2-[2-(4-cyclopropyl-phenyl)-1-oxo-2,8-diaza-spiro[4.5]dec-8-yl]-acetamide;
  2-[2-(4-Cyclopropyl-phenyl)-1-oxo-2,8-diaza-spiro[4.5]dec-8-yl]-N-(4-trifluoromethyl-benzyl)-acetamide;
  2-[2-(4-Cyclopropyl-phenyl)-1-oxo-2,8-diaza-spiro[4.5]dec-8-yl]-N-(4-fluoro-phenyl)-acetamide;
  3-[2-(4-Cyclopropyl-phenyl)-1-oxo-2,8-diaza-spiro[4.5]dec-8-yl]-N-(4-trifluoromethyl-benzyl)-propionamide;
  3-[2-(4-Cyclopropyl-phenyl)-1-oxo-2,8-diaza-spiro[4.5]dec-8-yl]-N-(4-fluoro-phenyl)-propionamide;
  2-(4-Cyclopropyl-phenyl)-8-(2-hydroxy-2-phenyl-ethyl)-2,8-diaza-spiro[4.5]decan-1-one;
  8-[2-(4-Chloro-phenyl)-2-hydroxy-ethyl]-2-(4-cyclopropyl-phenyl)-2,8-diaza-spiro[4.5]decan-1-one;
  2-[2-(4-Cyclopropyl-phenyl)-1-oxo-2,8-diaza-spiro[4.5]dec-8-yl]-N-(4-fluoro-phenyl)-propionamide;
  2-[2-(4-Cyclopropyl-phenyl)-1-oxo-2,8-diaza-spiro[4.5]dec-8-yl]-hexanoic acid butylamide;
  N-Butyl-2-[2-(4-cyclopropyl-phenyl)-1-oxo-2,8-diaza-spiro[4.5]dec-8-yl]-3-methyl-butyramide;
  2-(4-Cyclopropyl-phenyl)-8-((R)-2-hydroxy-2-phenyl-ethyl)-2,8-diaza-spiro[4.5]decan-1-one; and
  2-(4-Cyclopropyl-phenyl)-8-[(R)-2-(4-fluoro-phenyl)-2-hydroxy-ethyl]-2,8-diaza-spiro[4.5]decan-1-one.

15. A pharmaceutical composition comprising a compound according to claim 1 and a therapeutically inert carrier.

16. A compound according to claim 1 selected from the group consisting of:
  2-[2-(4-Cyclopropyl-phenyl)-1-oxo-2,8-diaza-spiro[4.5]dec-8-yl]-N-ethyl-acetamide;
  2-[2-(4-Cyclopropyl-phenyl)-1-oxo-2,8-diaza-spiro[4.5]dec-8-yl]-N,N-diethyl-acetamide;
  N-Butyl-2-[2-(4-cyclopropyl-phenyl)-1-oxo-2,8-diaza-spiro[4.5]dec-8-yl]-acetamide;
  2-[2-(4-Cyclopropyl-phenyl)-1-oxo-2,8-diaza-spiro[4.5]dec-8-yl]-N-(4-trifluoromethyl-benzyl)-acetamide;
  2-[2-(4-Cyclopropyl-phenyl)-1-oxo-2,8-diaza-spiro[4.5]dec-8-yl]-N-(4-fluoro-phenyl)-acetamide;
  2-(4-Cyclopropyl-phenyl)-8-(2-oxo-2-pyrrolidin-1-yl-ethyl)-2,8-diaza-spiro[4.5]decan-1-one;
  N-Benzyl-2-[2-(4-cyclopropyl-phenyl)-1-oxo-2,8-diaza-spiro[4.5]dec-8-yl]-N-methyl-acetamide;
  N-Cyclohexyl-2-[2-(4-cyclopropyl-phenyl)-1-oxo-2,8-diaza-spiro[4.5]dec-8-yl]-N-methyl-acetamide;
  2-[2-(4-Cyclopropyl-phenyl)-1-oxo-2,8-diaza-spiro[4.5]dec-8-yl]-N-(3-methoxy-propyl)-acetamide; and
  N-Butyl-3-[2-(4-cyclopropyl-phenyl)-1-oxo-2,8-diaza-spiro[4.5]dec-8-yl]-propionamide.

17. A compound according to claim 1 selected from the group consisting of:
  3-[2-(4-Cyclopropyl-phenyl)-1-oxo-2,8-diaza-spiro[4.5]dec-8-yl]-N-(4-trifluoromethyl-benzyl)-propionamide;
  3-[2-(4-Cyclopropyl-phenyl)-1-oxo-2,8-diaza-spiro[4.5]dec-8-yl]-N-(4-fluoro-phenyl)-propionamide;
  N-Benzyl-3-[2-(4-cyclopropyl-phenyl)-1-oxo-2,8-diaza-spiro[4.5]dec-8-yl]-N-methyl-propionamide;
  N-Cyclohexyl-3-[2-(4-cyclopropyl-phenyl)-1-oxo-2,8-diaza-spiro[4.5]dec-8-yl]-N-methyl-propionamide;
  2-(4-Cyclopropyl-phenyl)-8-(2-hydroxy-2-phenyl-ethyl)-2,8-diaza-spiro[4.5]decan-1-one;
  8-[2-(4-Chloro-phenyl)-2-hydroxy-ethyl]-2-(4-cyclopropyl-phenyl)-2,8-diaza-spiro[4.5]decan-1-one;
  2-[2-(4-Cyclopropyl-phenyl)-1-oxo-2,8-diaza-spiro[4.5]dec-8-yl]-N-(4-fluoro-phenyl)-propionamide;

2-[2-(4-Cyclopropyl-phenyl)-1-oxo-2,8-diaza-spiro[4.5]
dec-8-yl]-N-(4-fluoro-phenyl)-butyramide;

N-Butyl-2-[2-(4-cyclopropyl-phenyl)-1-oxo-2,8-diaza-
spiro[4.5]dec-8-yl]-propionamide; and N-Butyl-2-[2-(4-cyclopropyl-phenyl)-1-oxo-2,8-diaza-
spiro[4.5]dec-8-yl]-butyramide.

18. A compound according to claim 1 selected from the group consisting of:

N-Butyl-2-[2-(4-cyclopropyl-phenyl)-1-oxo-2,8-diaza-
spiro[4.5]dec-8-yl]-2-phenyl-acetamide;

2-[2-(4-Cyclopropyl-phenyl)-1-oxo-2,8-diaza-spiro[4.5]
dec-8-yl]-hexanoic acid butylamide;

N-Butyl-2-[2-(4-cyclopropyl-phenyl)-1-oxo-2,8-diaza-
spiro[4.5]dec-8-yl]-3-methyl-butyramide;

2-(4-Cyclopropyl-phenyl)-8-((S)-2-hydroxy-2-phenyl-
ethyl)-2,8-diaza-spiro[4.5]decan-1-one;

2-(4-Cyclopropyl-phenyl)-8-((R)-2-hydroxy-2-phenyl-
ethyl)-2,8-diaza-spiro[4.5]decan-1-one;

2-(4-Cyclopropyl-phenyl)-8-(2-hydroxy-2-phenyl-pro-
pyl)-2,8-diaza-spiro[4.5]decan-1-one;

2-(4-Cyclopropyl-phenyl)-8-[(R)-2-(4-fluoro-phenyl)-2-
hydroxy-ethyl]-2,8-diaza-spiro[4.5]decan-1-one;

8-[(R)-2-(3-Chloro-phenyl)-2-hydroxy-ethyl]-2-(4-cyclo-
propyl-phenyl)-2,8-diaza-spiro[4.5]decan-1-one;

2-(4-Cyclopropyl-phenyl)-8-[2-(3,4-dichloro-phenyl)-2-
hydroxy-ethyl]-2,8-diaza-spiro[4.5]decan-1-one; and 2-(4-Cyclopropyl-phenyl)-8-[2-(2,4-dichloro-phenyl)-2-
hydroxy-ethyl]-2,8-diaza-spiro[4.5]decan-1-one.

\* \* \* \* \*

UNITED STATES PATENT AND TRADEMARK OFFICE
CERTIFICATE OF CORRECTION

PATENT NO. : 8,389,539 B2  
APPLICATION NO. : 12/951095  
DATED : March 5, 2013  
INVENTOR(S) : Ackermann et al.

Page 1 of 1

It is certified that error appears in the above-identified patent and that said Letters Patent is hereby corrected as shown below:

On the title page, Item [54] and in the Specification at Column 1, line 1, Title should read as follows:

-- NEW AZACYCLIC DERIVATIVES --

On the title page, Item [73] Assignee should read as follows:

-- Hoffmann-La Roche Inc. --

Signed and Sealed this
Nineteenth Day of November, 2013

Teresa Stanek Rea
*Deputy Director of the United States Patent and Trademark Office*